(12) United States Patent
Davis

(10) Patent No.: US 9,055,808 B2
(45) Date of Patent: Jun. 16, 2015

(54) PORTABLE SELF POWERED LINE MOUNTABLE DEVICE FOR MEASURING AND TRANSMITTING THE UNDISTURBED CONDUCTOR TEMPERATURE OF ELECTRIC POWER LINE CONDUCTORS

(71) Applicant: Murray W. Davis, Grosse Pointe Woods, MI (US)

(72) Inventor: Murray W. Davis, Grosse Pointe Woods, MI (US)

( * ) Notice: Subject to any disclaimer, the term of this patent is extended or adjusted under 35 U.S.C. 154(b) by 0 days.

(21) Appl. No.: 14/096,460

(22) Filed: Dec. 4, 2013

(65) Prior Publication Data

US 2014/0177672 A1  Jun. 26, 2014

Related U.S. Application Data

(60) Provisional application No. 61/740,517, filed on Dec. 21, 2012.

(51) Int. Cl.
| | | |
|---|---|---|
| *G01K 1/08* | (2006.01) | |
| *G01K 1/14* | (2006.01) | |
| *G01K 13/00* | (2006.01) | |
| *A46B 9/02* | (2006.01) | |
| *H02G 1/02* | (2006.01) | |
| *G01B 11/06* | (2006.01) | |
| *G01W 1/14* | (2006.01) | |
| *G01R 1/20* | (2006.01) | |
| *G01R 19/00* | (2006.01) | |
| *G01R 31/08* | (2006.01) | |
| *G01N 27/22* | (2006.01) | |
| *H01F 38/30* | (2006.01) | |
| *H04N 5/225* | (2006.01) | |
| *G01D 11/30* | (2006.01) | |
| *H01F 27/02* | (2006.01) | |
| *H01F 27/22* | (2006.01) | |
| *H01R 4/28* | (2006.01) | |
| *G01R 1/22* | (2006.01) | |

(52) U.S. Cl.
CPC ............ *A46B 9/028* (2013.01); *Y10T 29/49117* (2015.01); *H02G 1/02* (2013.01); *G01B 11/0616* (2013.01); *G01W 1/14* (2013.01); *G01R 1/20* (2013.01); *G01R 19/0092* (2013.01); *G01R 31/08* (2013.01); *G01N 27/223* (2013.01); *G01R 19/0084* (2013.01); *H01F 38/30* (2013.01); *H04N 5/2252* (2013.01); *G01D 11/30* (2013.01); *G01K 13/00* (2013.01); *H01F 27/02* (2013.01); *H01F 27/22* (2013.01); *H01R 4/28* (2013.01); *A46B 2200/3073* (2013.01); *G01R 1/22* (2013.01)

(58) Field of Classification Search
USPC ......................................... 374/152, 208, 141
See application file for complete search history.

(56) References Cited

U.S. PATENT DOCUMENTS

| | | |
|---|---|---|
| 2,303,824 A | 12/1942 | Comins |
| 2,306,117 A | 12/1942 | Dunlap |

(Continued)

FOREIGN PATENT DOCUMENTS

| | | |
|---|---|---|
| CN | 202041573 | 11/2011 |
| JP | 2003-061752 | 9/2004 |

*Primary Examiner* — Mirellys Jagan
(74) *Attorney, Agent, or Firm* — Carlson, Gaskey & Olds, P.C.

(57) ABSTRACT

A device for attaching to a power line conductor includes a jaw assembly and at least one jaw slot formed on a portion of the jaw assembly configured to engage a stranded power line conductor. The at least one jaw slot extends at an angle on the jaw assembly configured to match a helical angle of strands on an outer surface of the stranded power line conductor and configured to space the jaw assembly from at least one strand of the stranded power line conductor.

24 Claims, 28 Drawing Sheets

(56) References Cited

U.S. PATENT DOCUMENTS

| | | |
|---|---|---|
| 3,267,507 A | 8/1966 | Cox |
| 3,622,867 A | 11/1971 | Topper et al. |
| 3,861,197 A | 1/1975 | Adler |
| 4,032,842 A | 6/1977 | Green et al. |
| 4,052,000 A | 10/1977 | Honikman |
| 4,061,963 A | 12/1977 | Green |
| 4,234,863 A | 11/1980 | Shumway et al. |
| 4,242,930 A | 1/1981 | Myers et al. |
| 4,268,818 A | 5/1981 | Davis et al. |
| 4,326,316 A | 4/1982 | Dolenti |
| 4,420,752 A | 12/1983 | Davis et al. |
| 4,546,340 A | 10/1985 | Kuchuris |
| 4,728,887 A | 3/1988 | Davis |
| 4,746,241 A | 5/1988 | Burbank |
| 4,801,937 A | 1/1989 | Fernandes |
| 4,806,855 A | 2/1989 | Davis |
| 4,827,272 A | 5/1989 | Davis |
| 5,029,101 A | 7/1991 | Fernandes |
| 5,140,257 A * | 8/1992 | Davis ............................ 324/106 |
| 5,232,518 A | 8/1993 | Nath et al. |
| 5,341,088 A | 8/1994 | Davis |
| 5,351,359 A | 10/1994 | Golden |
| 5,426,360 A * | 6/1995 | Maraio et al. ................. 324/126 |
| 5,883,511 A | 3/1999 | Foster |
| 6,151,065 A | 11/2000 | Steed et al. |
| 6,157,160 A | 12/2000 | Okawa et al. |
| 6,299,824 B1 | 10/2001 | Mayr et al. |
| 6,713,670 B2 | 3/2004 | Stern et al. |
| 6,741,069 B1 | 5/2004 | Klemar et al. |
| 6,924,732 B2 | 8/2005 | Yokoo |
| 6,983,508 B2 | 1/2006 | Saurer |
| 7,030,593 B2 | 4/2006 | Pinkerton et al. |
| 7,127,972 B2 | 10/2006 | Klein et al. |
| 7,310,109 B2 | 12/2007 | Dottling et al. |
| 7,412,338 B2 | 8/2008 | Wynans et al. |
| 7,432,787 B2 | 10/2008 | Muench et al. |
| 7,545,140 B2 | 6/2009 | Humphreys et al. |
| 7,557,563 B2 | 7/2009 | Gunn et al. |
| 7,570,045 B2 * | 8/2009 | Wolfe et al. .................... 324/127 |
| 7,579,824 B2 | 8/2009 | Rea |
| 7,706,596 B2 | 4/2010 | Garvey |
| 8,022,291 B2 | 9/2011 | Thomsen et al. |
| 8,144,445 B2 | 3/2012 | Caggiano et al. |
| 8,184,015 B2 | 5/2012 | Lilien et al. |
| 8,203,328 B2 * | 6/2012 | Bose et al. ................. 324/117 H |
| 8,300,922 B1 | 10/2012 | Garvey, III |
| 8,320,146 B2 | 11/2012 | Haines et al. |
| 8,322,332 B2 | 12/2012 | Rogers |
| 8,400,504 B2 | 3/2013 | Al-Duwaish et al. |
| RE44,256 E * | 6/2013 | Bright et al. ................... 324/512 |
| 8,536,857 B2 | 9/2013 | Nero, Jr. |
| 8,628,211 B2 | 1/2014 | Jensen et al. |
| 8,686,302 B2 | 4/2014 | Brasher et al. |
| 2004/0012678 A1 | 1/2004 | Li |
| 2006/0060007 A1 | 3/2006 | Mekhanoshin |
| 2006/0125469 A1 | 6/2006 | Hansen |
| 2008/0077336 A1 | 3/2008 | Fernandes |
| 2008/0136403 A1 | 6/2008 | Deck |
| 2008/0297162 A1 | 12/2008 | Bright |
| 2009/0207421 A1 | 8/2009 | Kelly et al. |
| 2009/0212241 A1 | 8/2009 | McGeoch |
| 2009/0243876 A1 | 10/2009 | Lilien et al. |
| 2010/0085036 A1 | 4/2010 | Banting et al. |
| 2010/0192975 A1 | 8/2010 | Schweikert |
| 2011/0204879 A1 | 8/2011 | Peretto |
| 2011/0308566 A1 | 12/2011 | Johnson |
| 2012/0086804 A1 | 4/2012 | Ishibashi et al. |
| 2012/0152346 A1 | 6/2012 | Yang et al. |
| 2013/0022078 A1 * | 1/2013 | Phillips et al. ................ 374/179 |
| 2013/0179079 A1 | 7/2013 | Lancaster |
| 2014/0110376 A1 | 4/2014 | Zahlmann et al. |

* cited by examiner

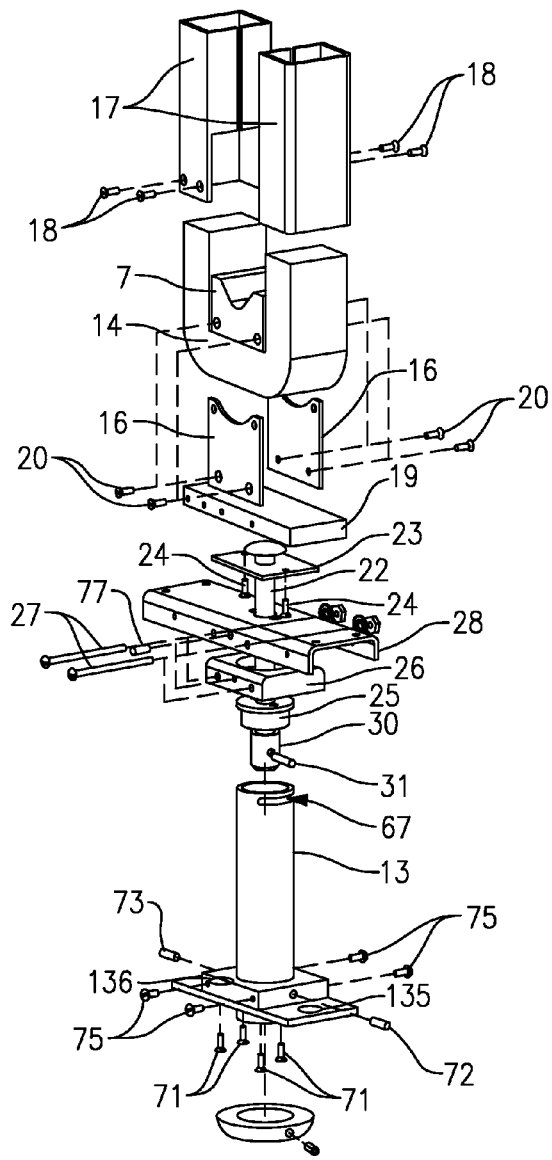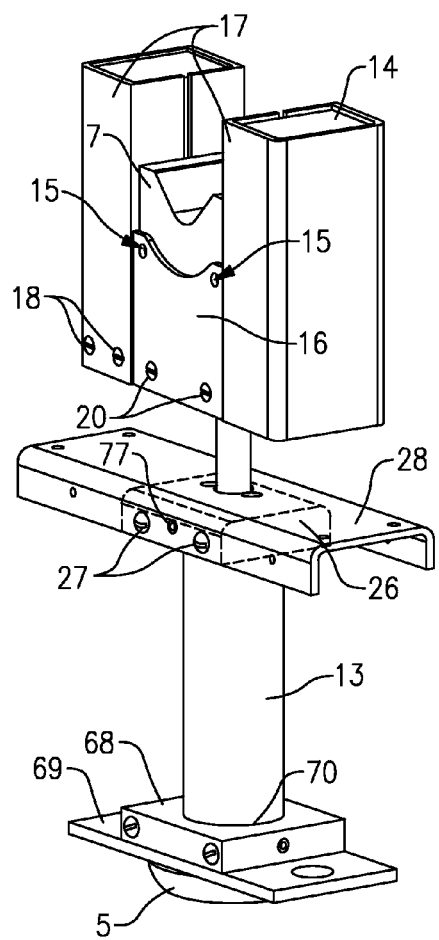
FIG.10
FIG.11

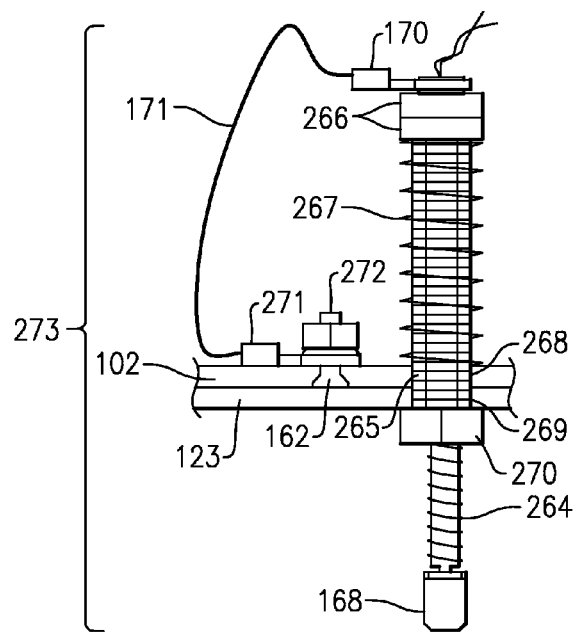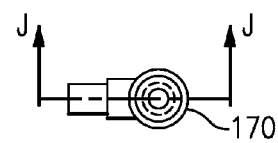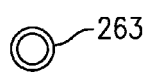
FIG. 22
FIG. 25
FIG. 26
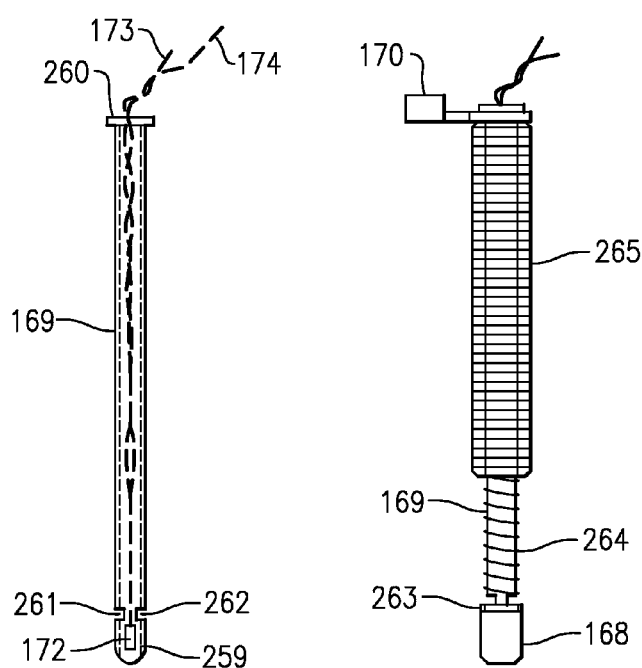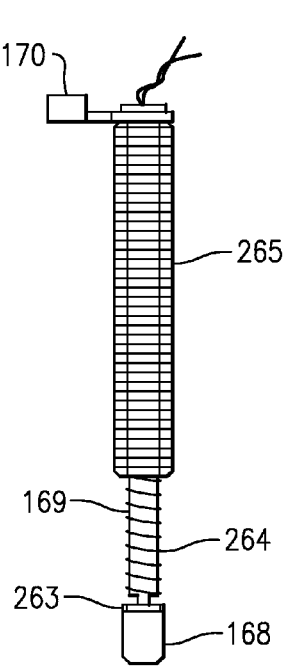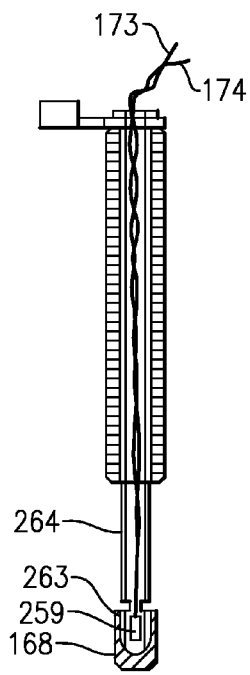
FIG. 23
FIG. 24
FIG. 27

PORTABLE SELF POWERED LINE MOUNTABLE DEVICE FOR MEASURING AND TRANSMITTING THE UNDISTURBED CONDUCTOR TEMPERATURE OF ELECTRIC POWER LINE CONDUCTORS

CROSS REFERENCE TO RELATED APPLICATION

This application claims reference to U.S. Provisional Application No. 61/740,517 dated Dec. 21, 2012.

BACKGROUND

The present disclosure relates to a multiple parameter sensor-transmitter/receiver unit which may be installed on or removed from an energized electric power line, such as an overhead power line. With the advent of Smart-Grid applications for electric power systems, there is an ever increasing need for a device that measures electric, mechanical, and environmental parameters of the power line.

In order to address the increasing need for monitoring power lines, devices have been developed that attach directly to the power line. These devices generally require a power source, such as batteries or solar panels. When utilizing batteries, regular maintenance must be performed to replace the batteries, which can become costly. When solar panels are used, the device may only be powered during sunny weather conditions and during daylight hours. Therefore, there is a need for a device which is low maintenance and can be constantly powered independent of weather conditions.

Electric power line conductors are usually stranded conductors including a number of strands of wire wrapped into a concentrically wound complete cylindrical conductor. This is done to introduce flexibility into large diameter conductors. Large diameter solid conductors are not used because they are too rigid for line conductors. When a device for measuring the conductor temperature of a stranded conductor carrying current is physically placed onto the conductor the surface conductor temperature will be lowered at the location of said device on the conductor, because the temperature of this device is lower than the conductor temperature of the line and the heat generated within the conductor due to the $I^2R$ (current squared times conductor resistance) losses will be conducted away from the conductor and onto the device where the heat is then thermally radiated and convected away into the lower temperature ambient or environment.

The most important parameter in determining the real time current carrying capacity of an overhead electric power line is the conductor temperature. This is one of the parameters used to determine (1) the thermal state of the overhead line conductor, (2) the line sag including elevated temperature creep (which causes the line to permanently increase in length due to high conductor temperature operation), (3) the loss of conductor tensile strength, and (4) the temperature effect on line hardware such as conductor dead ends connected to the line supporting structures and the line splices connecting the conductors together. Having an accurate method of measuring the conductor temperature insures the line does not sag down beyond the minimum clearance of the power line to the earth or to an object under the line, because as the line heats up due to the current flowing in the line, the conductor elongates due to thermal expansion. Also, the maximum allowable current, or the thermal rating of the line, is limited by the maximum conductor temperature so that both the line clearance is not exceeded due to increased sag and the loss of conductor tensile strength criteria is not exceeded. Therefore, there is a need for a device which is low maintenance and can be provide an undisturbed conductor temperature reading.

SUMMARY

A device for attaching to a power line conductor includes a jaw assembly and at least one jaw slot formed on a portion of the jaw assembly configured to engage a stranded power line conductor. The at least one jaw slot extends at an angle on the jaw assembly configured to match a helical angle of strands on an outer surface of the stranded power line conductor and configured to space the jaw assembly from at least one strand of the stranded power line conductor.

A device for attaching to a power line conductor includes a jaw assembly for engaging a power line conductor. The jaw assembly includes at least one upper jaw and at least one lower jaw. The at least one upper jaw having a contact surface with a first slope. A jaw insert is located adjacent the at least one upper jaw. The jaw insert includes a second contact surface having a second slope. The first slope is greater than the second slope.

BRIEF DESCRIPTION OF THE DRAWINGS

FIG. 10 illustrates an expanded view of the lower magnetic core, example lead screw assembly, and an example hotstick guide tube.

FIG. 11 illustrates the collapsed view of the lower magnetic core, the lead screw assembly, and the hotstick guide tube.

FIG. 22 illustrates an example conductor temperature sensor probe assembly installed on an example upper jaw holder and keeper.

FIG. 23 illustrates an example protection tube and temperature sensor with leads.

FIG. 24 illustrates the protection tube, an example threaded nipple, an example shoe, an example compression spring, an example isolation washer, the temperature sensor, and an example ring connector.

FIG. 25 illustrates a top view of FIG. 24.

FIG. 26 illustrates a top view of the isolation washer.

FIG. 27 illustrates a sectional view taken along line J-J of FIG. 25.

DETAILED DESCRIPTION

Figure 1:
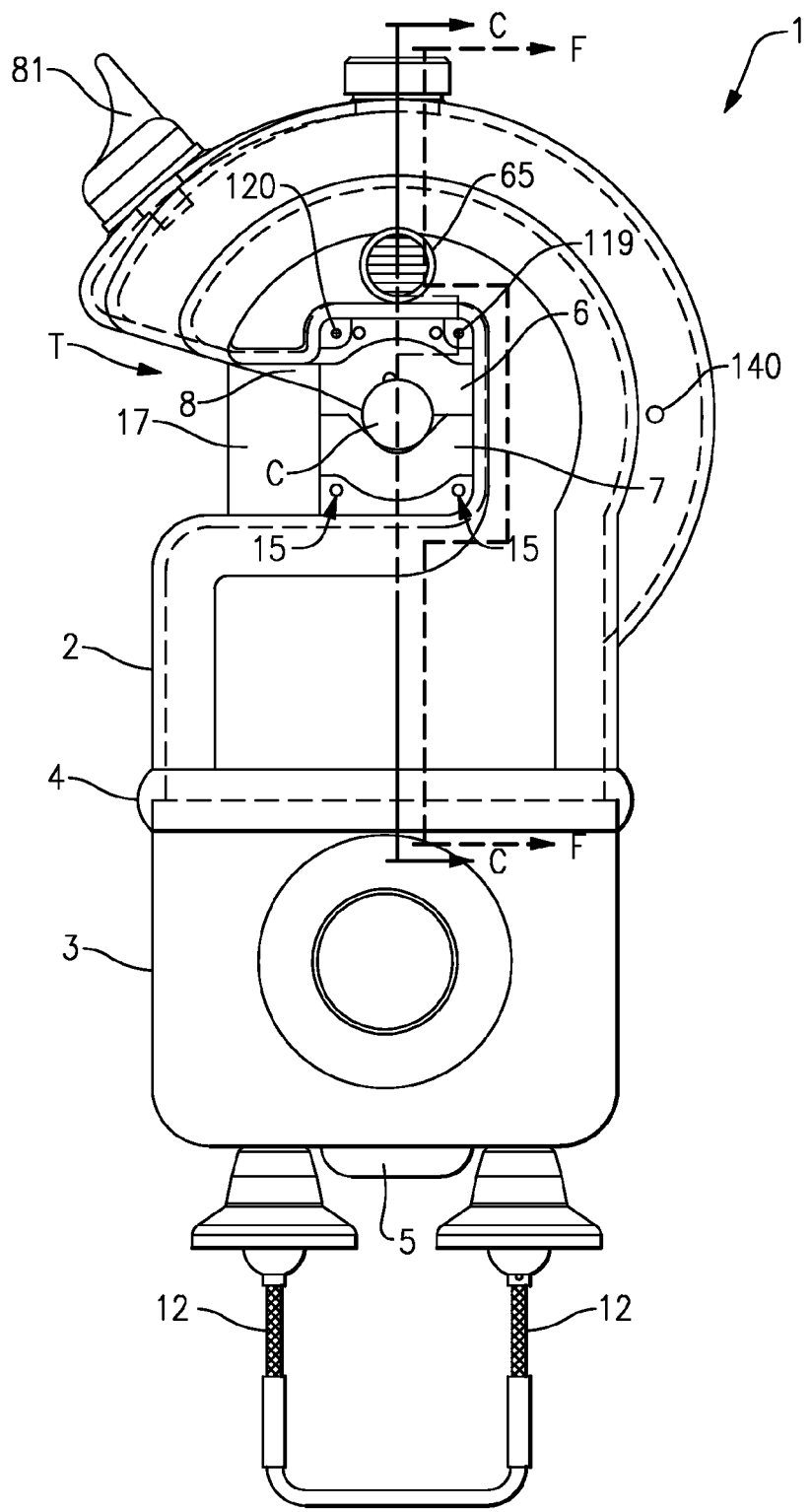
FIG. 1 illustrates a right side view of an example sensor transmitter receiver unit ("STR unit").
Figure 2:
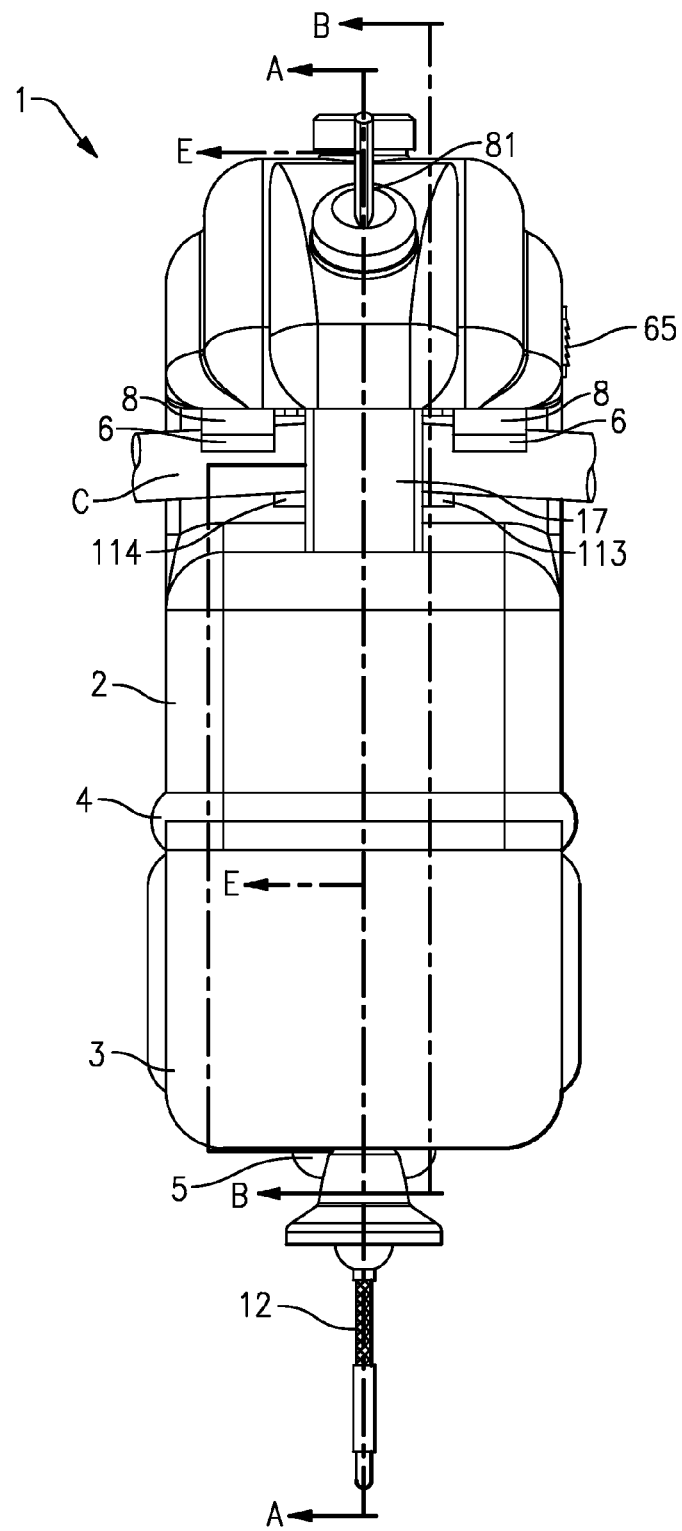
FIG. 2 illustrates a front view of the STR unit of FIG. 1.

FIGS. 1 and 2 illustrate an example sensor transmitter receiver unit ("STR unit") 1 installed on a power line conductor C for measuring and monitoring various parameters of the power line conductor C and its environment. The STR unit 1 is formed from a one piece upper housing 2 and a one piece lower housing 3. The lower housing 3 is accepted into a bead 4 formed on a distal end of the upper housing 2. In this example, the bead 4 which is an integral part of the upper housing 2 is formed by machining a portion of the upper housing 2 to form a groove on the inside of the bead 4. The lower housing 3 is secured to the bead 4 and the upper housing 2 by a collar 5. The collar 5 attaches to a hotstick guide tube 13 (FIG. 3) that is secured to the upper housing 2 and extends through the lower housing 3.

In one example, the upper housing 2 and the lower housing 3 are made of aluminum or other suitable electrically conductive material. The material chosen should accommodate subassembly installation without the use of external surface fasteners which could generate corona discharges due to high voltage being applied to the upper housing 2 and the lower housing 3. The upper housing 2 has the advantage of reducing the number of mating surfaces and eliminating mismatches between multiple cast parts which can generate corona discharges and audible noise due to slightly offset sharp edges of the mating surfaces of the adjacent castings.

Figure 3:
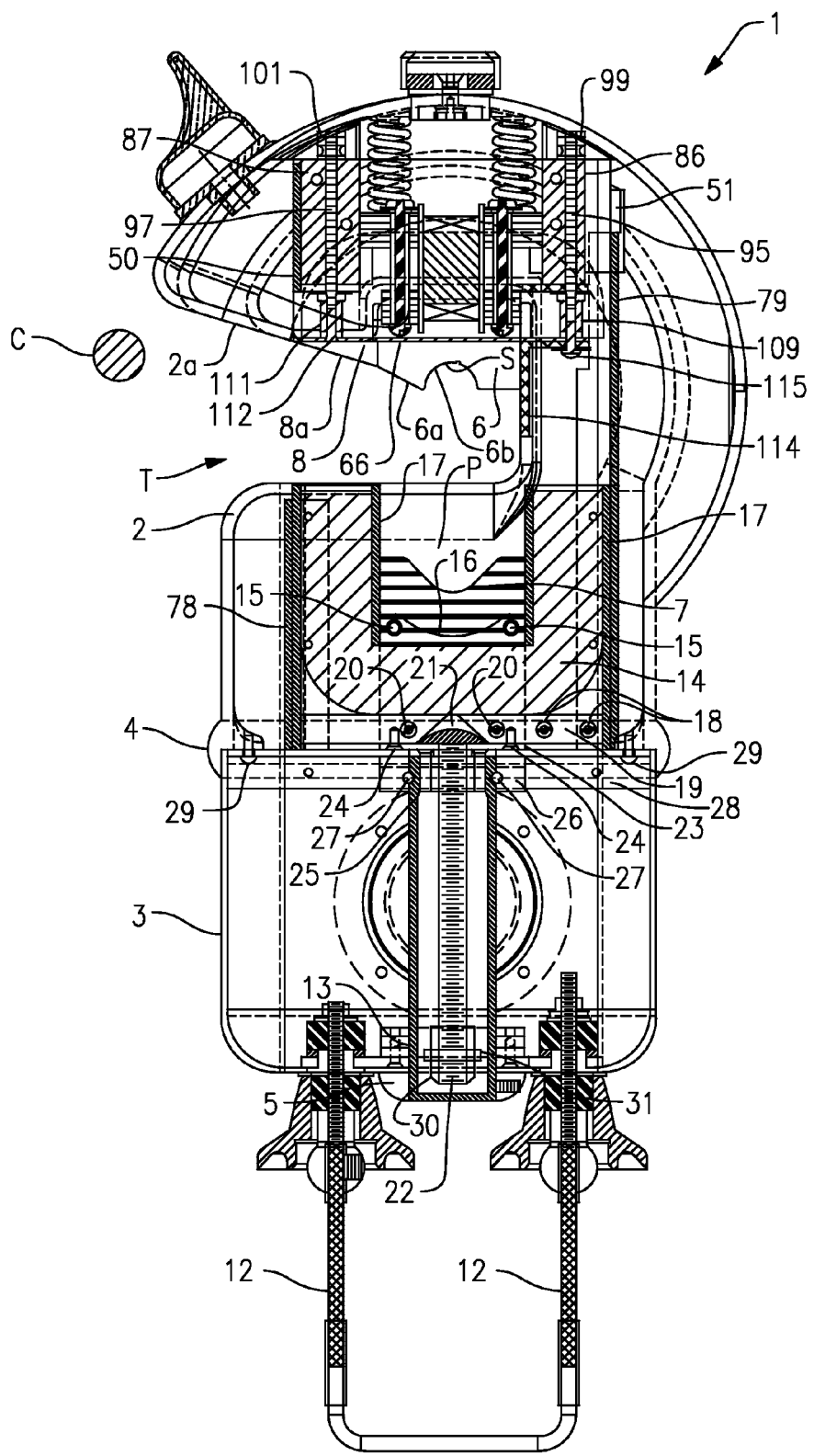
FIG. 3 illustrates a cross-sectional view taken along line A-A of FIG. 2.
Figure 4:
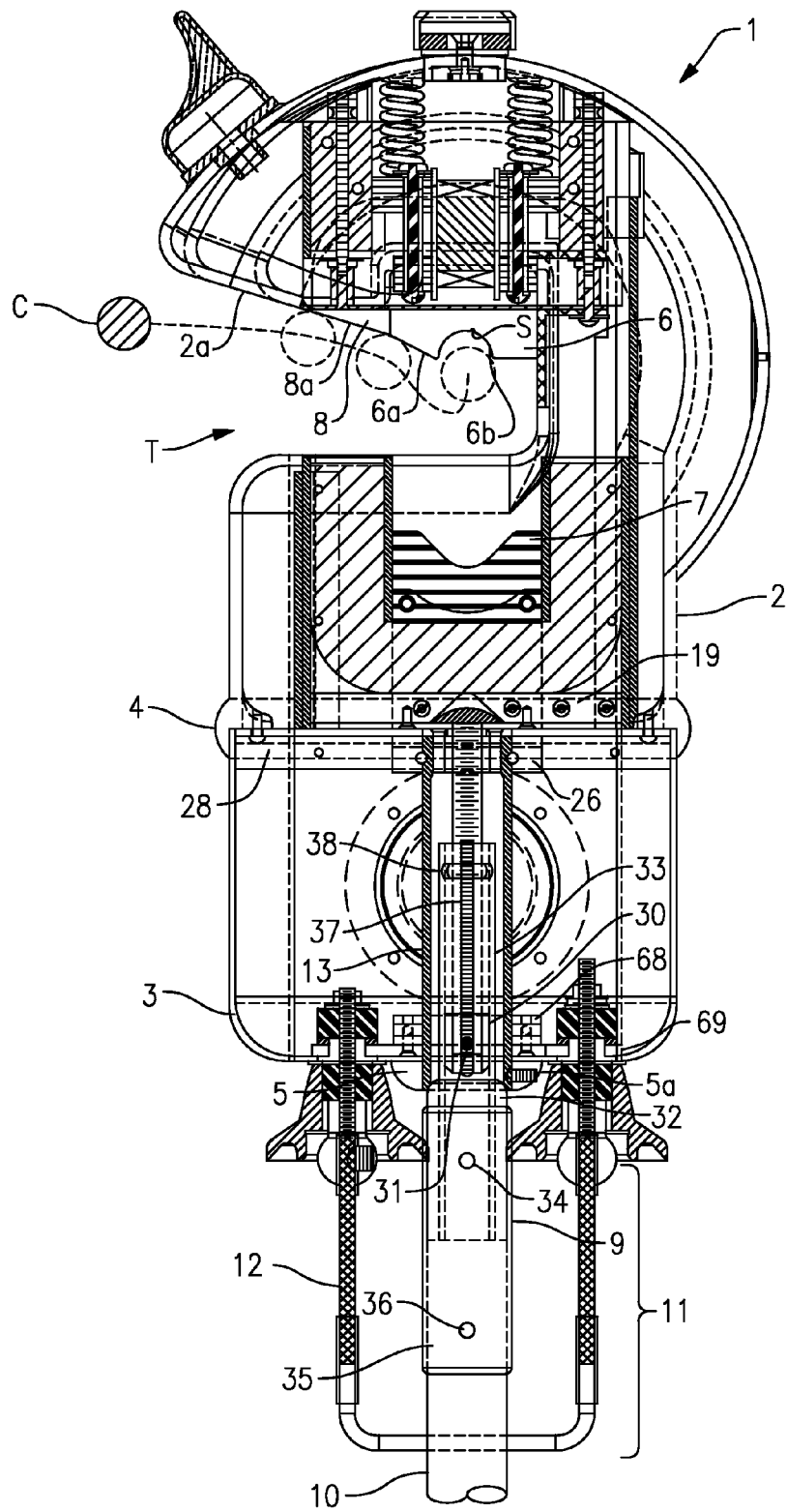
FIG. 4 illustrates a cross-sectional view taken along line A-A of FIG. 2 with an example hotstick.

Referring to FIGS. 3 and 4, before the STR unit 1 is clamped onto the conductor C, a lower jaw 7 is moved to its fully lowered position spaced from upper jaws 6. This allows the conductor C to pass from position "A" of FIG. 3 through a throat T on the left side of the upper housing 2 and onto the upper jaws 6 in position "B" as shown in FIG. 5.

With the lower jaw 7 of the STR unit 1 in its fully lowered position, a specially designed hotstick 10 is inserted into the bottom of the STR unit 1 and inside the hotstick guide tube 13. In this example, the hotstick 10 is made of an electrically insulated material such as fiberglass. The hotstick 10 includes a hotstick driver assembly 9 (FIG. 4) attached to the hotstick 10 with a pin 36. The hotstick 10 provides the required electrical insulation between the hands of the linemen and the energized conductor C. A flexible stirrup assembly 11 (FIG. 4) contains a flexible braided conductor 12 which bends out of the way to allow the hotstick driver assembly 9 to enter a hole in the collar 5. As mentioned earlier, the collar 5 secures the lower housing 3 to the bead 4 on the upper housing 2. The collar 5 is fastened to the hotstick guide tube 13 using the set screw 5a which is screwed into the collar 5 and into a hole in the hotstick guide tube 13.

With the hotstick 10 and the hotstick driver assembly 9 fully engaged inside the hotstick guide tube 13, the STR unit 1 can be lifted by the lineman with the hotstick 10 onto the conductor C while maintaining the STR unit 1 securely attached to the hotstick 10.

Figures 5, 5A:
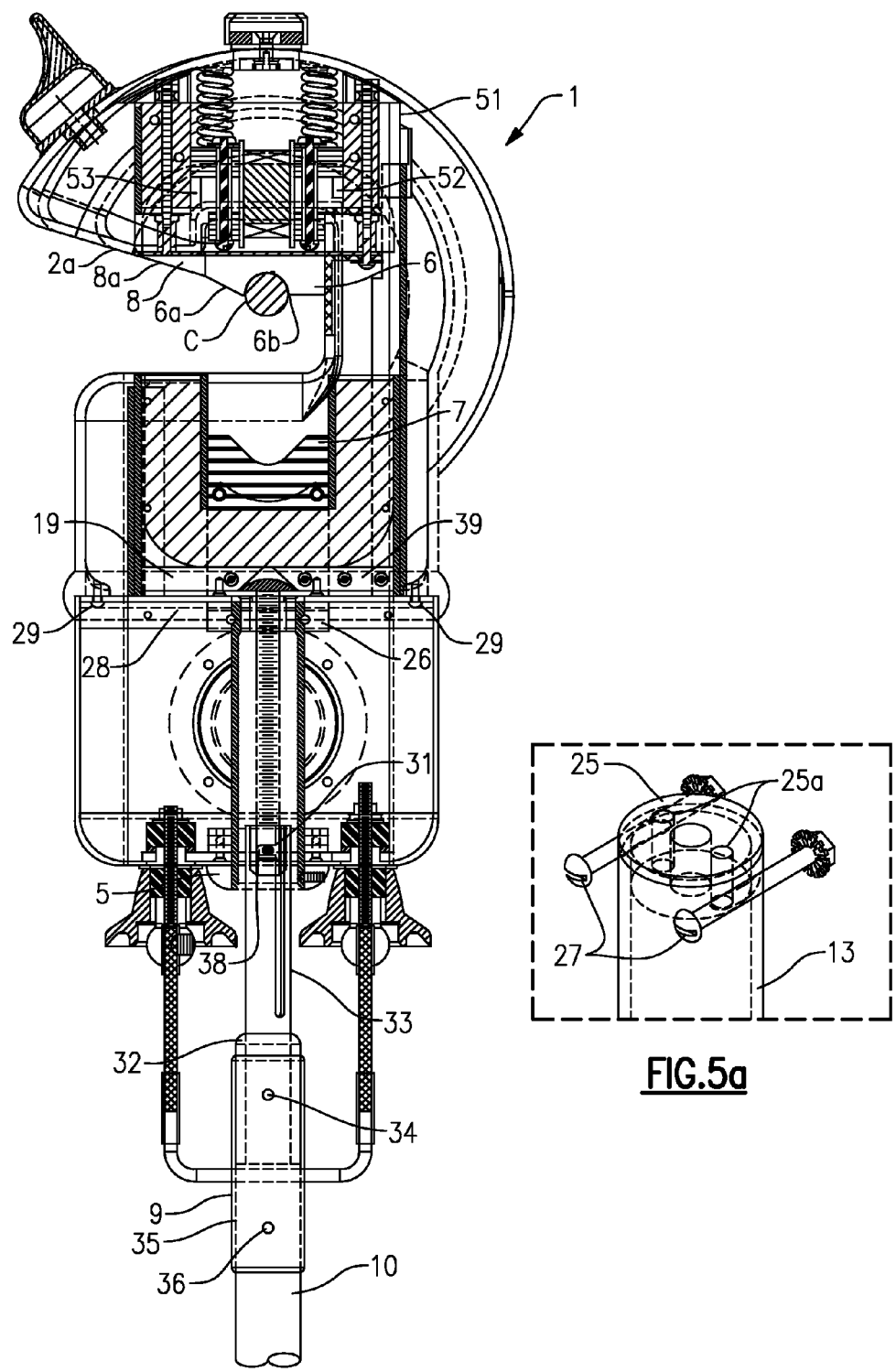
FIG. 5 illustrates another cross-sectional view taken along line A-A of FIG. 2 with the example hotstick.
FIG. 5a illustrates an enlarged view of a keyhole slot.
Figure 14:
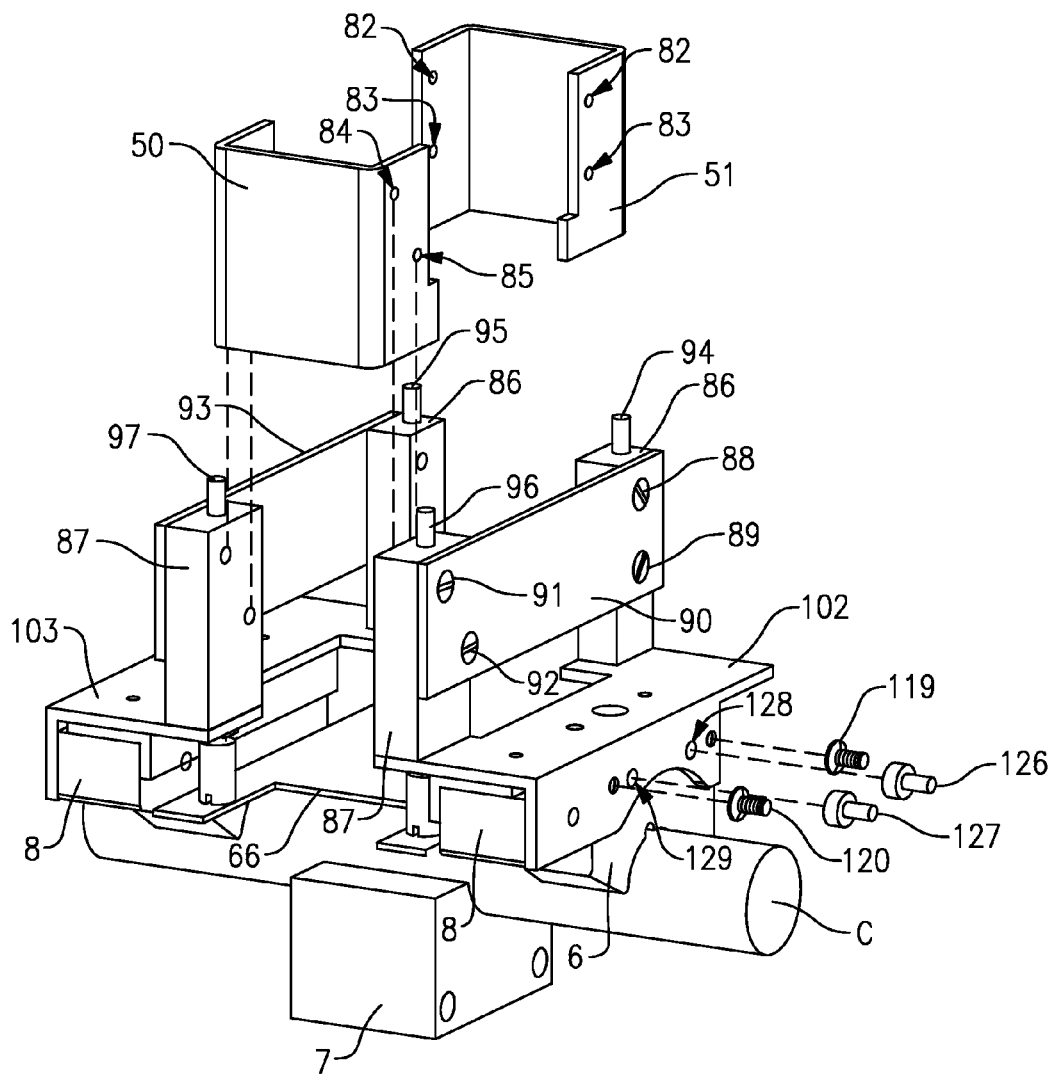
FIG. 14 illustrates an exploded view of example support blocks mounting the upper magnetic core subassembly and example upper and lower jaws.

The upper housing 2 includes two jaw inserts 8, shown in FIGS. 5 and 14, located adjacent the throat T and the upper jaws 6. The two jaw inserts 8 include inclined surfaces 8a and the upper jaws 6 include inclined surfaces 6a. The angle of incline of the inclined surfaces 8a matches the angle of the incline of an inclined surface 2a on the upper housing 2.

The angle of the inclined surfaces 6a is steeper than the angle of the inclined surfaces 8a and the inclined surface 2a to aid in installing the STR Unit 1 on the conductor C. As the conductor C slides across the inclined surfaces 2*a* and 8*a* and reaches the steeper incline of the inclined surface 6*a*, the STR unit 1 will bounce slightly upward and land in a circular notch 6*b* of the upper jaws 6 (See FIG. 4). This allows a conductor temperature sensor to be mounted vertically and in the middle inside the upper jaws 6 and initially extends slightly below the circular notch 6*b* for the upper portion of the conductor C. The two different inclined surfaces 6*a* and 8*a* of the jaw inserts 8 and upper jaws 6 prevent the conductor temperature sensor S, shown in FIGS. 3 and 4, from becoming damaged since the conductor C firmly lands vertically in the circular notch 6*b* of the upper jaws 6 and pushes the conductor temperature sensor S up to the inside surface of the circular notch 6*b*.

In FIG. 3, the lower jaw 7 is located in a pocket P between two legs of a lower magnetic core 14. The lower jaw 7 is held in place with two spring pins 132 and 133 (FIG. 15) located in the lower jaw 7 that snap into two holes 15 in a lower jaw holder 16 (FIGS. 10 and 11) which is attached to a bottom block 19 using two screws 20 (FIG. 3). The bottom block 19 is located adjacent the base of the upper housing 2.

Two identical electrically conductive lower core covers 17 partially surround the two legs of the lower magnetic core 14. The lower core covers 17 are attached to the bottom block 19 on each side of the lower jaw holder 16 using screws 18 of FIG. 3 on the front right side and one set of the screws 18 on the back left side (not shown). The front and back lower jaw holders 16 are both held in place by the four screws 20, two in the front and two in the back. The two legs of the lower magnetic core 14 are totally encased by the two lower core covers 17 and the front and back lower jaw holders 16. Therefore, the lower magnetic core 14 is not exposed to any moisture, such as from rain, snow, and ice that could enter through the throat T of the upper housing 2 (FIG. 3).

The bottom block 19 contains a conical hole 21 in the center which provides a very low friction bearing surface for the semi-circular top of a lead screw 22 (FIG. 3). The lead screw 22 is held in the conical hole 21 with a retainer plate 23 which has a hole in the middle the size of the lead screw 22 diameter and is fastened to the bottom block 19. The lead screw 22 is threaded into the center of a threaded bushing 25. The threaded bushing 25 has a reduced diameter cylindrical lower portion which fits inside the hotstick guide tube 13 and a larger diameter cylindrical top portion of the threaded bushing 25 is supported on the upper end of the hotstick guide tube 13. Both the threaded bushing 25 and the hotstick guide tube 13 are attached to a hotstick guide support 26 using two large through bolts 27 and nuts which are placed through the holes in a bottom support 28.

Referring to FIG. 2, the upper jaws 6 include two spaced apart jaws and the lower jaw 7 includes a single jaw aligned between the two spaced apart upper jaws 6. When lower jaw 7 is clamped onto the conductor C, the conductor C is bent slightly upward as the lower jaw 7 extends upward between the upper jaws 6 creating a bending moment in the conductor C. The bending moment in the conductor C prevents the STR unit 1 from sliding down the conductor C, especially when the STR unit 1 is mounted at the point of attachment adjacent a utility pole or tower where the slope of the conductor C is at its maximum value. Preventing the upper jaws 6 and the lower jaw 7 from sliding down the conductor C at the point of attachment is necessary when the STR unit is being used to measure sag of the power line conductor.

Referring to FIGS. 5 and 5*a*, the bottom support 28 includes an upside down "U" shaped cross member and is fastened at each end to the upper housing with two large threaded screws 29 on each side. The threaded bushing 25 has two small vertical holes 25*a* drilled through the threaded bushing 25 on each side of the threaded hole in the middle for the lead screw 22. The vertical holes 25*a* are countersunk on the top and provide drainage paths for fluid, such as rain water, that can accumulate underneath the bottom block 19 and on top of the bottom support 28 (FIG. 5*a*). The water then drains through the two vertical holes 25*a* in the threaded bushing 25 and drops on the inside of the hotstick guide tube 13 and out the bottom of the STR unit 1. Therefore, water will not leak into the lower housing 3.

Figure 6:
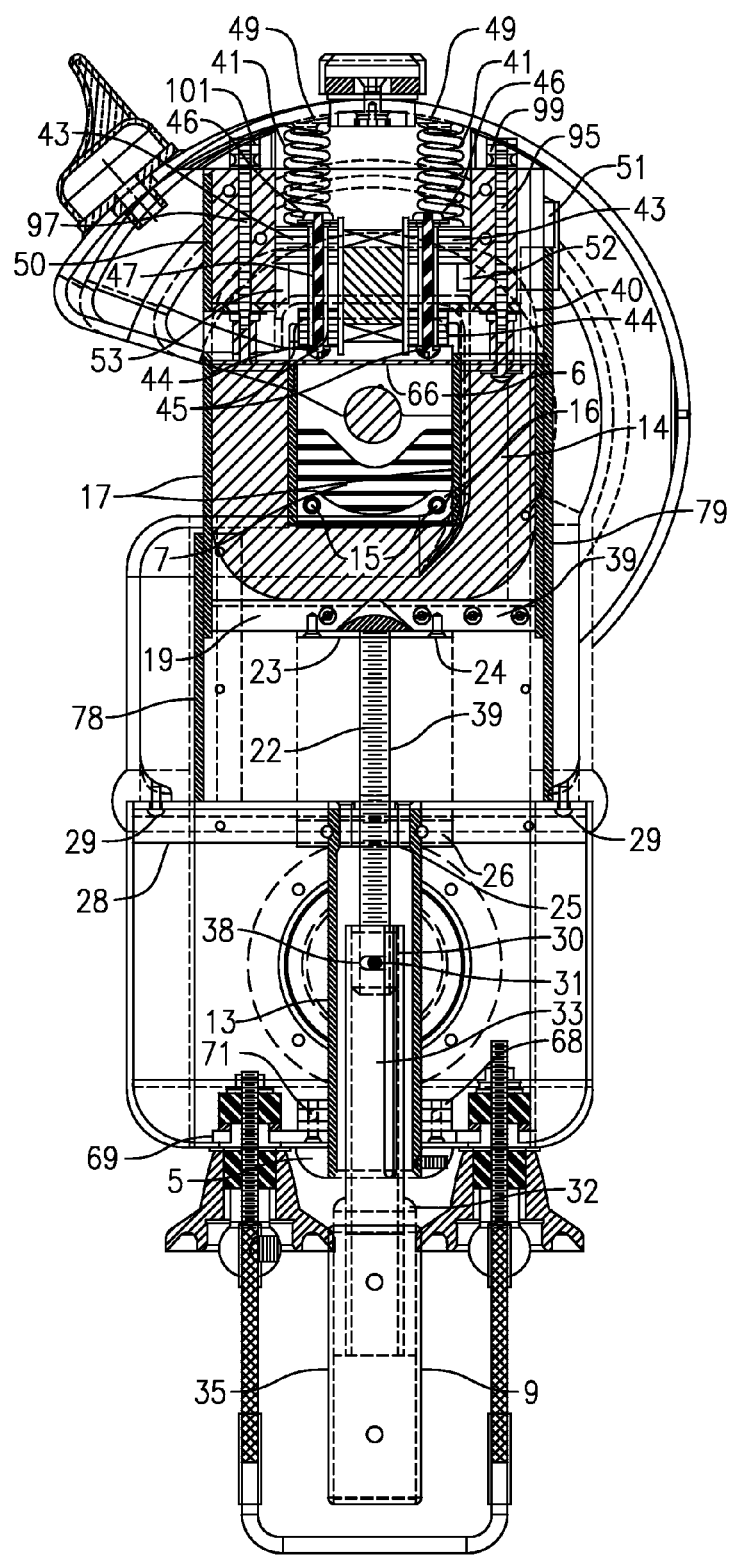
FIG. 6 illustrates another cross-sectional view taken along line A-A of FIG. 2 engaging a conductor.

Referring to FIG. 6, the lead screw 22 has a small diameter hotstick guide 30 which is threaded on the inside and is screwed on the bottom of the lead screw 22. A pin 31 keeps the hotstick guide 30 from turning on the lead screw 22. The hotstick guide 30 prevents the inside of a hotstick lead screw driver 33 from coming into contact with the threads on the lead screw 22 and damaging the internal bore of the lead screw driver 33. It also guides the lead screw driver 33 onto the lead screw 22. When the pin 31 engages the lead screw driver 33 the STR unit 1 is ready for installation on the conductor C.

The hotstick driver assembly 9 includes the lead screw driver 33, a hotstick driver coupling 32, a rivet 34, a hotstick sleeve 35, the pin 36, and the hotstick 10. The hotstick 10 of FIG. 4 rests on the rounded portion of the hotstick driver coupling 32 and the rounded inside bottom of the hotstick guide tube 13. This prevents the lead screw driver 33 from applying pressure to the threaded bushing 25 upon installation of the STR unit 1 on the conductor C. The lead screw driver 33 and the hotstick driver coupling 32 are each fastened to the hotstick sleeve 35 by the rivet 34 and the hotstick sleeve 35 is attached to the hotstick 10 with the pin 36. A long narrow vertical slot in the lead screw driver 33 allows the pin 31 of the lead screw 22 to be engaged with the lead screw driver 33 and is free to slide up or down in the vertical slot 37 as the lead screw is turned to tighten the lower jaw 7 on the conductor C or to loosen the lower jaw 7 from the conductor C to remove the STR unit 1.

When the hotstick driver assembly 9 is engaged with the lead screw 22 as shown in FIG. 4, the STR unit 1 is raised to position "A" relative to the height of the conductor C. The STR unit 1 is then moved toward the conductor C so that the conductor C passes through the throat T of the upper housing 2 and into position "B" as shown in FIG. 5. Once the STR unit 1 is fully supported by the conductor C in position "B", the hotstick driver assembly 9 is turned clockwise by the installer with the hotstick 10 and allowed to drop down from its position in FIG. 4 to a lower position as in FIG. 5. A horizontal keyhole slot 38 of the lead screw driver 33 is now engaged with the pin 31 of the lead screw 22. With the pin 31 in the horizontal keyhole slot 38, the hotstick driver assembly 9 and the hotstick 10 are secured to the STR unit 1.

In this example, an opening and closing mechanism 39 of FIG. 6 extends the lower jaw 7 upward to secure the STR unit 1 on the conductor C. Additionally, the opening and closing mechanism 39 can also retract the lower jaw 7 to remove the STR unit 1 from the conductor C. The opening and closing mechanism 39 includes the lower magnetic core 14, the lower core covers 17, the lower jaw holders 16, the lower jaw 7, spring pins 132 and 133, the bottom block 19, the retainer plate 23, two fasteners 24, the lead screw 22, the hotstick guide 30, and the pin 31.

FIG. 6 illustrates the keyhole slot 38 on the lead screw driver 33 engaged with the pin 31 on the lead screw 22. As the lead screw 22 is turned clockwise, the opening and closing mechanism 39 moves the lower magnetic core 14 toward an upper magnetic core 40. The upper magnetic core 40 has two large compression springs 41 to bias the upper magnetic core 40 downward. The compression springs 44 provide pressure to hold both the upper magnetic core 40 and the lower magnetic core 14 together to reduce the magnetic reluctance caused by air gaps 54 (FIG. 8) between the upper magnetic core 40 and the lower magnetic core 14.

The hotstick driver assembly 9 can continue to be turned clockwise even after the lower magnetic core 14 begins to mate with the upper magnetic core 40 because the compression springs 41 compress at the top of the upper magnetic core 40. The clockwise motion of the hotstick driver assembly 9 can be achieved either manually or with a battery powered drill or another rotating device, until the lower jaw 7 is tightened onto the conductor C. After the STR unit 1 is mounted on the conductor C, the hotstick 10 is turned slightly to the left, or counterclockwise, and the pin 31 will become disengaged from the horizontal portion of the keyhole slot 38. The hotstick 10 is then free to be removed when the pin 31 aligns with the vertical slot 37.

Figure 7:
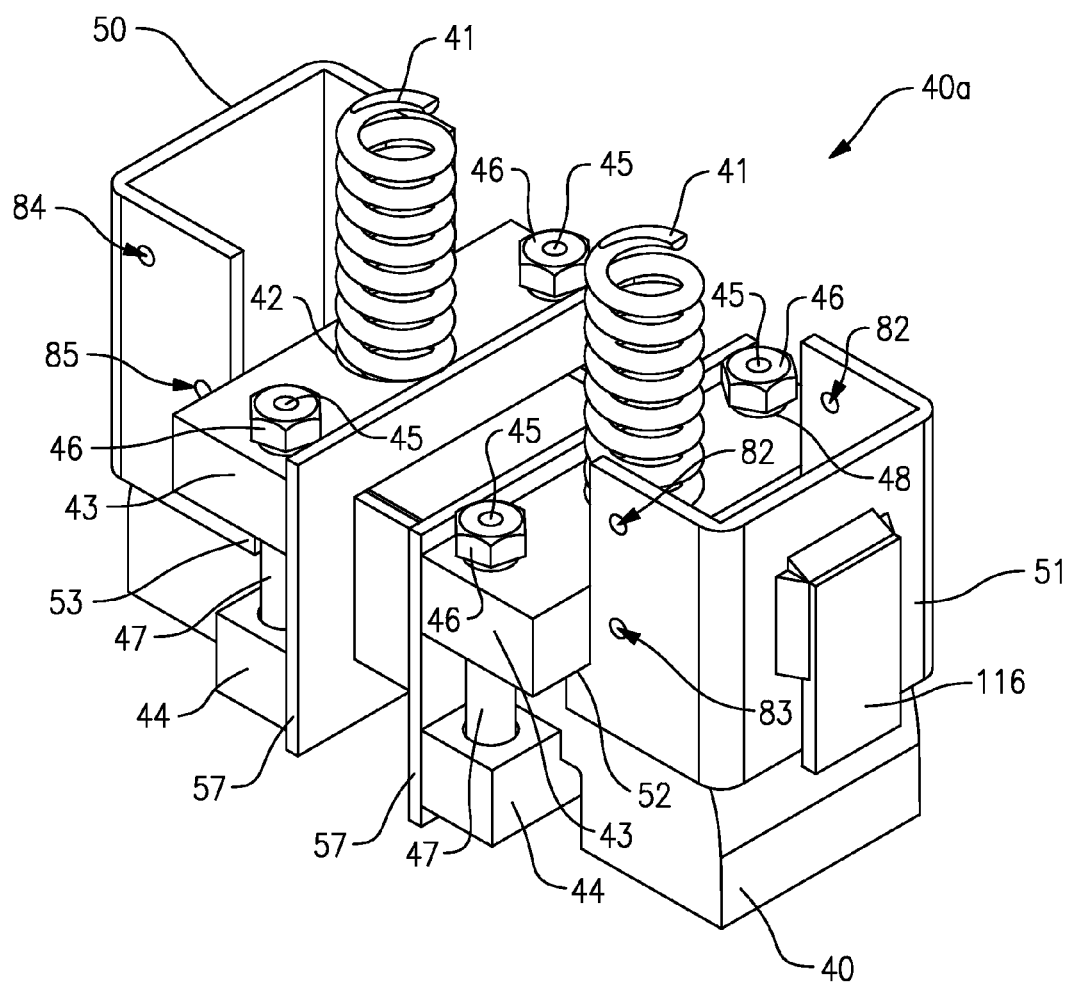
FIG. 7 illustrates an example upper magnetic core subassembly.
Figure 8:
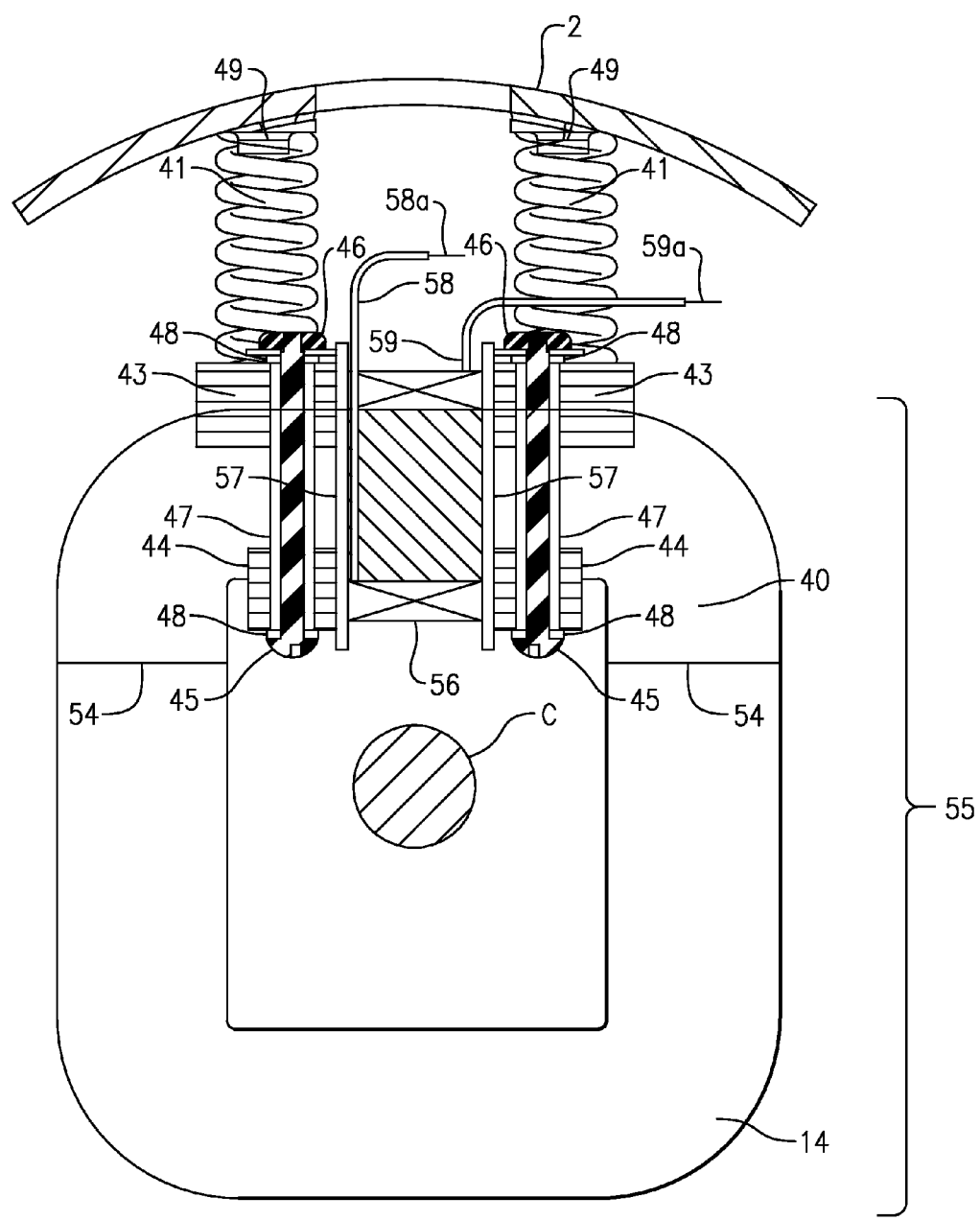
FIG. 8 illustrates an expanded view of an example upper magnetic core and an example lower magnetic core surrounding the conductor and an example power supply transformer.

FIGS. 7 and 8 illustrate the bottom of the compression springs 41 are held in alignment in two cylindrical pockets 42 of two identical horizontal upper core blocks 43 which are each used to clamp the upper magnetic core 40 to two identical magnetic horizontal lower core blocks 44. The top of the compression springs 41 are held in place with two projections 49 extending downward on the inside of the upper housing 2. The compression springs 41 are totally enclosed by the upper housing 2 and are protected from the adverse weather which can cause corrosion. The air gaps 54 between the upper and lower magnetic cores 40 and 14 are totally enclosed by the upper housing 2 which prevents the air gaps 54 from becoming corroded due to moisture from the environment. The horizontal upper core blocks 43 and the horizontal lower core blocks 44 are clamped around the upper magnetic core 40 on each side using two through bolts 45 and two nuts 46 in the front and two through bolts 45 and two nuts 46 located in the back of the upper horizontal core blocks 43 and horizontal lower core blocks 44.

When the two large compression springs 41 push the upper core blocks 43 down, the upper magnetic core 40 is prevented from falling out of a left core shoe 50 and a right core shoe 51, by a step 52 located at the bottom of the right core shoe 51 and a step 53 located at the bottom of the left core shoe 50.

When the lower magnetic core 14 mates with the upper magnetic core 40, the lead screw 22 can be turned further clockwise to move the two upper core blocks 43 away from the steps 52 and 53 and further compress the compression springs 41. The lead screw 22 can continue to be turned clockwise and compress the compression springs 41 until the lower jaw 7 and the upper jaws 6 are tight on the conductor C.

Electrical insulating spools 47 are inserted over each of the through bolts 45 and electrical insulating washers 48 are inserted under the head of each through bolt 45 and under each nut 46. The insulating spools 47 and the insulating washers 48 on each of the through bolts 45 prevent shorted electrically conductive paths around the upper magnetic core 40 which is comprised of the four through bolts 45, four nuts 46, the two electrically conductive upper core blocks 43 and the two lower core blocks 44.

When the upper jaws 6 and the lower jaw 7 are firmly tightened on the conductor C, the compression springs 41 are compressed to their maximum distance, and thus the maximum compressive force is also applied to the lower magnetic core 14 and the upper magnetic core 40. This decreases the size of the air gaps 54 between the lower magnetic core 14 and the upper magnetic core 40 and the magnetic reluctance between the lower magnetic core 14 and the upper magnetic core 40. Depending on the size of the conductor C, varying amounts torque can be applied to the hotstick driver assembly 9 to tighten the opening and closing mechanism 39 on the conductor C.

The physical size and shape of the upper jaws 6 and the lower jaw 7 are designed such that approximately the same compressive force is applied to the upper magnetic core 40 and the lower magnetic core 14. In one example, there are five different sets of upper and lower jaws 6 and 7 that can fit different conductor sizes and types ranging from 0.162 inches in diameter and up to 1.17 inches in diameter. The opening and closing mechanism 39 allows the STR unit 1 to be installed on a wide range of conductor diameters without changing the upper jaws 6 and the lower jaws 7 while maintaining sufficient contact between the upper magnetic core 40 and the lower magnetic core 14 to complete the magnetic circuit of the power supply transformer 55 of the STR unit 1 which derives its power from the current flowing through the conductor C to power a power supply module 60 of FIG. 9. Because the STR unit 1 derives power from the conductor C, batteries or solar cells are not required to power the STR unit 1. The STR unit 1 is powered at all times when current is flowing in the conductor C, even at current levels as low as 6.8 amperes and still process data and transmit data at 1 watt power levels because of the low threshold of the power supply module 60.

Maintaining a minimum magnetic reluctance insures that a power supply transformer 55 (FIGS. 8 and 9) will provide the needed secondary voltage $V_2$ and secondary current $I_2$ to operate the power supply transformer 55, sensor electronics module 63, and transmitter/receiver 64. The power supply transformer 55 includes the upper magnetic core 40, the lower magnetic core 14, and a coil winding 56. The upper magnetic core and the lower magnetic core form a window W for accepting the conductor C.

Figure 12:
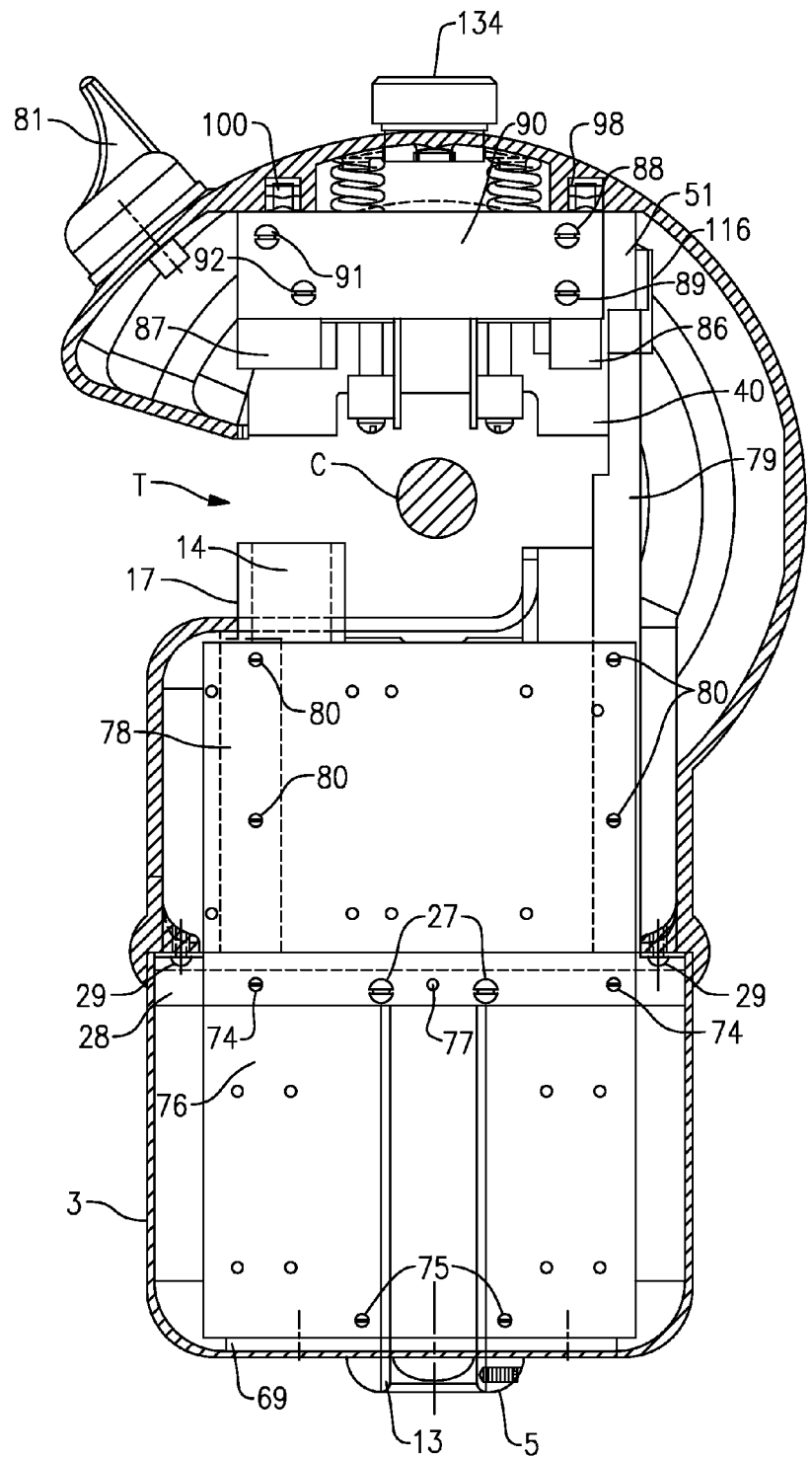
FIG. 12 illustrates a cross-sectional view taken along line B-B of FIG. 2.

The number of secondary turns $N_2$ of wire on the coil winding 56 are optimized to produce the required secondary voltage $V_2$ and secondary current $I_2$ with a minimum of current $I_1$ in the conductor C. The coil winding 56 is held in place by two coil bobbins 57 which are supported laterally by the two upper core blocks 43 and the two lower core blocks 44. Secondary leads 58*a* and 59*a* of coil windings 58 and 59, respectively, are connected to the power supply module 60 which maintains the same level of secondary voltage across leads 61 and 62 for the sensor electronics module 63 and the transmitter/receiver 64 even though the primary current may range from 34 amperes up to 1000 amperes. Lower primary currents of 6.8 amperes are achievable with the low threshold current power supply module 60. The power supply module 60 contains an energy storage device 256 (FIG. 13) which can power the transmitter/receiver 64 when the conductor C current ceases to flow. A transmitting and receiving antenna 81 for the on-board transmitter/receiver 64 is mounted on the upper housing 2 (FIG. 12).

Locating the coil winding 56, 58, and 59 on the upper magnetic core 40 allows the heat from the coil winding 56, 58, and 59 to escape through a vent 65 (FIG. 1) in the upper housing 2. When the conductor sensor S located within the STR unit 1 measures the temperature of the conductor C, it is important that the heat from the coil windings 56, 58, and 59 does not affect the temperature of the conductor C or the conductor temperature sensor S, which is in electrical communication with the sensor electronics module 63. As shown in FIG. 6, a thermally insulating barrier 66 located below the coil windings 56, 58, and 59, allows for a more accurate temperature reading of the conductor temperature by blocking heat from the coil windings 56, 58, and 59.

FIGS. 10-12 and 13 illustrate the lower magnetic core 14 with the lower core covers 17, the lead screw 22, the hotstick guide tube 13, and other related parts in both exploded and collapsed views. The hotstick guide tube 13 is anchored at the top with the through bolts 27 that extend through the bottom support 28 and the hotstick guide support 26. A round cylindrical milled slot 67 is located along opposing sides of the top of the hotstick guide tube 13 to accept the through bolts 27 that support the hotstick guide tube 13.

A central hole 70 extends through a base plate support 68 and a base plate 69 for accepting a bottom portion of the hotstick guide tube 13. The base plate support 68 and the base plate 69 are connected to each other with four identical threaded screws 71. The hotstick guide tube 13 is attached to the base plate support 68 and the base plate 69 with set screws 72 and 73. Left and right side panels 76 of FIG. 12 are attached to the base plate support 68 and the bottom support 28 for the lower core 14 with the use of two identical screws 74 extending through the bottom support 28 and the side panel 76 and at the bottom with two identical screws 75 extending through the side panel 76 and the base plate support 68.

The threaded bushing 25 rests on top of the hotstick guide tube 13 and is prevented from turning relative to the hotstick guide tube 13 using a set screw 77. The left and right side panels 76 not only provide added strength, but also provide the physical space to mount the power supply module 60, the transmitter/receiver 64, the sensor electronics 63, and support left and right lower core guides 78 and 79.

The left lower core guide 78 and a right lower core guide 79 are "U" shaped and guide the opening and closing mechanism 39 such that the lower magnetic core 14 is aligned with the upper magnetic core 40. Each of the left and right lower core guides 78 and 79 are attached to the left and right side panels 76 with four threaded screws 80. The lower housing 3 is placed over the hotstick guide tube 13 at the bottom and fitted up to the base plate 69 and held in place with the collar 5. This means that once the collar 5 is removed, the lower housing 3 can be removed thus allowing access to the power supply module 60, sensor electronics module 63, and the transmitter/receiver 64 of FIG. 9 mounted inside and on the left and right side panels 76 for easy maintenance and repair.

FIGS. 7 and 12-15 illustrate an upper magnetic core subassembly 40a mounted to the upper housing 2. The left and right core shoes 50 and 51 support the upper magnetic core 40 such that the upper magnetic core 40 can move freely up and down inside the left and right shoes 50 and 51. The left and right core shoes 50 and 51 are attached to the upper housing 2 using four support blocks 86 and 87 of FIG. 14, right and left upper core guides 90 and 93, and four vertical through bolts 94, 95, 96, and 97.

Figure 13:
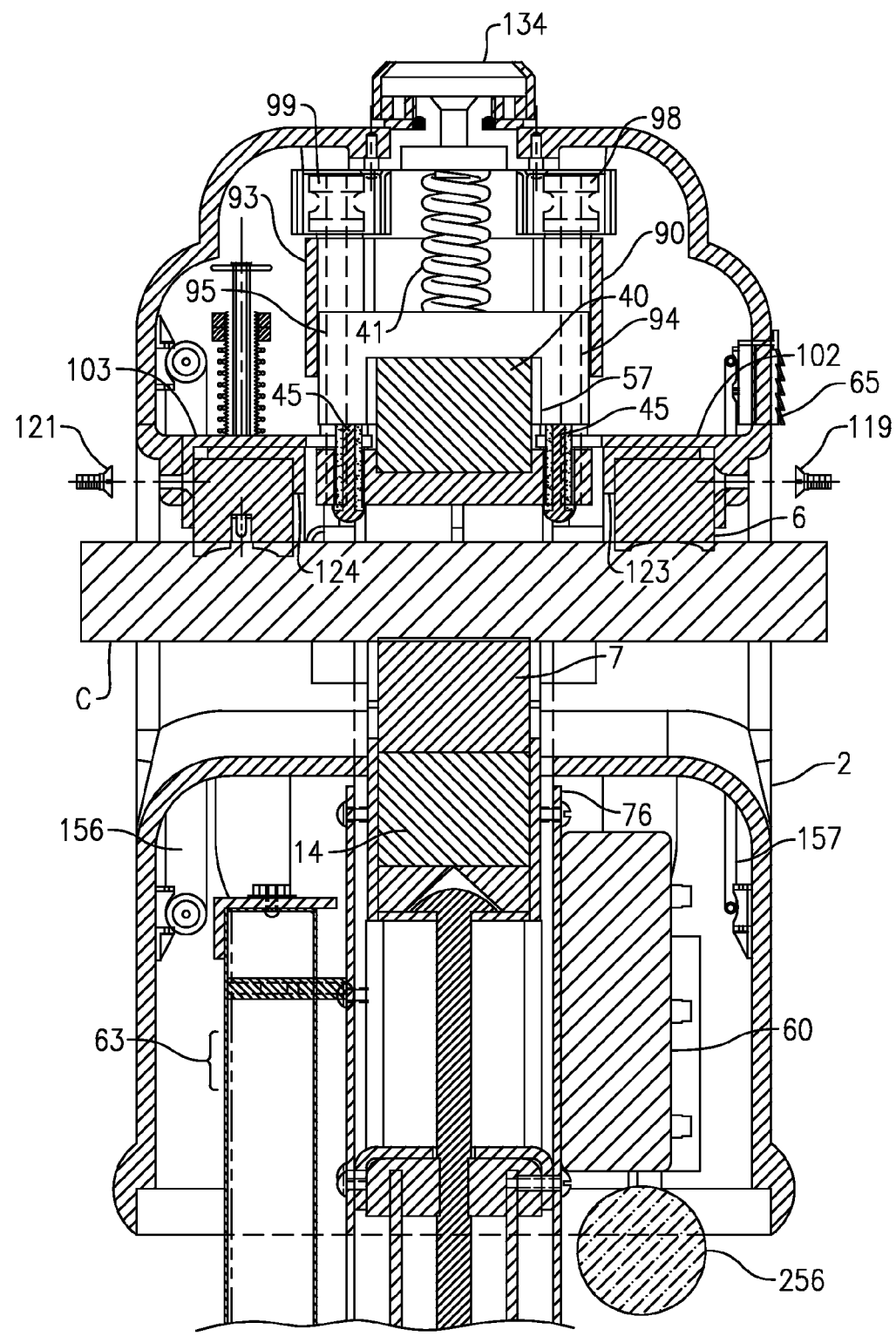
FIG. 13 illustrates a cross-sectional view taken along line C-C of FIG. 1.

The upper magnetic core subassembly 40a can be inserted through the throat T and fastened to the inside of the upper housing 2. A top portion of the upper housing 2 is "C" shaped which provides a surface on the inside for mounting a "C" loop coil 156 for measuring the power line frequency current (60 Hz or 50 Hz) and a "C" loop coil 157 for measuring lightning stroke current (FIGS. 13 and 16).

The right core shoe 51 has two identical threaded holes 82 and 83 on the front and back for a total of four, and left core shoe 50 has two identical threaded holes 84 and 85 on the front and back for a total of four as shown in FIGS. 7 and 14. As shown in FIG. 14, two identical support blocks 86 on the right side are placed on the front and back of the right core shoe 51 and two identical support blocks 87 are placed on the front and back of the left core shoe 50.

To align the two right side support blocks 86 with the two sets of threaded holes 82 and 83 on the right side of the right core shoe 51, threaded screws 88 and 89 are first inserted into the upper and lower holes in the right side upper core guide 90 and then through the two holes in the right support block 86 and screwed into the accommodating threaded holes 82 and 83 of the right core shoe 51. The two left side support blocks 87 are held in alignment with the left core shoe 50 by first inserting two threaded screws 91 and 92 through the other end of the right side upper core guide 90 and then through the holes in the left side support block 87 and screwed into the threaded holes 84 and 85 of the left core shoe 50. The same process is repeated on the back side by connecting support blocks 86 and 87 to the left upper core guide 93 with the backside of the right core shoe 51 and the back side of the left core shoe 50.

The purpose of the upper core guides 90 and 93 is to insure the two long vertical through bolts 94 and 95 placed through the vertical holes in the two right side support blocks 86 and two long vertical through bolts 96 and 97 placed through the vertical holes in the two left side support blocks 87 line up with the four threaded holes in four threaded inserts 98, 99, 100, and 101, which are embedded in the casting of the upper housing 2. The two right side support blocks 86 are prevented from falling down by inserting the back of a right side upper jaw holder 102 and the back of the left side upper jaw holder 103 over the vertical through bolts 94 and 95 and threading nuts 104 and 105 onto the two vertical through bolts 94 and 95 and tightening them down, respectively. The two left side support blocks 87 are held in place by inserting the vertical through bolts 96 and 97 through the front hole in the right side upper jaw holder 102 and the front hole in the left side upper jaw holder 103 and threading two nuts 106 and 107 on the vertical through bolts 96 and 97 and tightening them down, respectively.

Four threaded through standoffs 108, 109, 110, and 111 are screwed onto the four vertical through bolts 94, 95, 96, and 97, respectively. The thermal barrier 66 is placed over the four bottom holes of the standoffs 108, 109, 110, and 111 and screwed to the standoffs 110 and 111 on the front left side with two flat head screws 112 as shown in FIG. 15.

Figure 15:
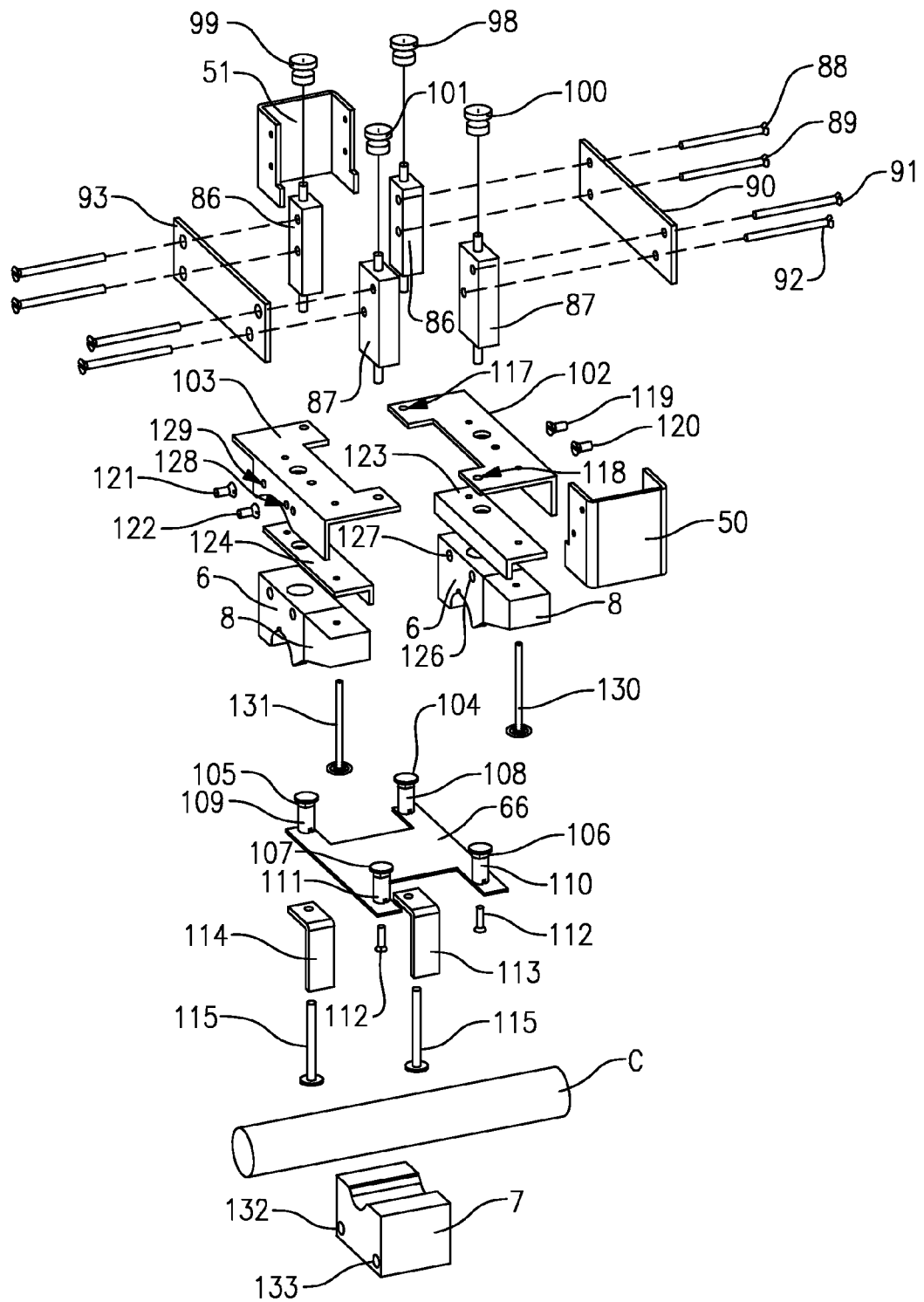
FIG. 15 illustrates an exploded view of an upper magnetic core mount and the upper and lower jaws.

FIGS. 2 and 15 illustrate casting fillers 113 and 114 located on the back left and back right sides of the STR unit 1 and secured with round head screws 115 which are first inserted through holes in the casting fillers 113 and 114 and then through the two back holes on the right and left side of the thermal barrier 66 and into the standoffs 108 and 109, respectively.

After the upper magnetic core subassembly 40a is mounted, the left and right lower core guides 78 and 79 including the opening and closing mechanism subassembly 39 and the left and right side panels 76 are inserted through the bottom of the upper housing 2 (See FIG. 12). Four screws 29 are inserted through the two holes on the left and the two holes on the right of the bottom support 28 and screwed into the threaded holes of the upper housing 2. It should be noted that during the insertion process, the right lower core guide 79, shown in FIG. 12, slides around the outside surface of the right core shoe 51 and underneath a tab 116 at the top as a weldment on the right upper side of the right core shoe 51.

As shown in FIG. 12, the tab 116 insures that the right lower core guide 79 fits precisely around the outside of the right core shoe 51 to provide a near perfect alignment of the lower magnetic core 14 with the upper magnetic core 40. The precise alignment between the upper magnetic core 40 and the lower magnetic core 14 reduces magnetic reluctance by decreasing the air gaps 54. This results in a decrease in the threshold current for the operation of the power supply module 60.

Referring to FIGS. 14 and 15, the right side upper jaw holder 102 and the left side upper jaw holder 103 support the two upper jaws 6 and the jaw inserts 8. The long vertical through bolts 96 and 97 which are screwed into the threaded inserts 100 and 101 at the top and on the inside of the upper housing 2 fit through top holes 117 and 118 on the back and front of the right side upper jaw holder 102 on the right side. Also, flush mount screws 119 and 120 are inserted on the back and through corresponding holes in the right side upper jaw holder 102 and are screwed into the upper housing. The flush mount screws 119 and 120 are installed before the upper jaws 6 and inserts 8 are mounted to the right side upper jaw holder 102. The same arrangement for mounting the left side upper jaw holder 103 is followed using screws 121 and 122.

Right and left upper jaw keepers 123 and 124 prevent the upper jaws 6 from dropping down on the inside, because spring pins 126 and 127 are located on the outside and when depressed snap into the holes 128 and 129 of the right side upper jaw holder 102. The same procedure is followed with the left upper jaw keeper 124.

The jaw inserts 8 on the right and left sides of the STR unit 1 and in front of the upper jaws 6 are held in place by inserting threaded bolts 130 and 131 into each insert 8 and through the right and left keepers 123 and 124 and screwing into the upper jaw holders 102 and 103. The spring pins 132 and 133 are included in the lower jaw 7 which when depressed snap into the two holes 15 in the lower jaw holder 16.

Figure 9:
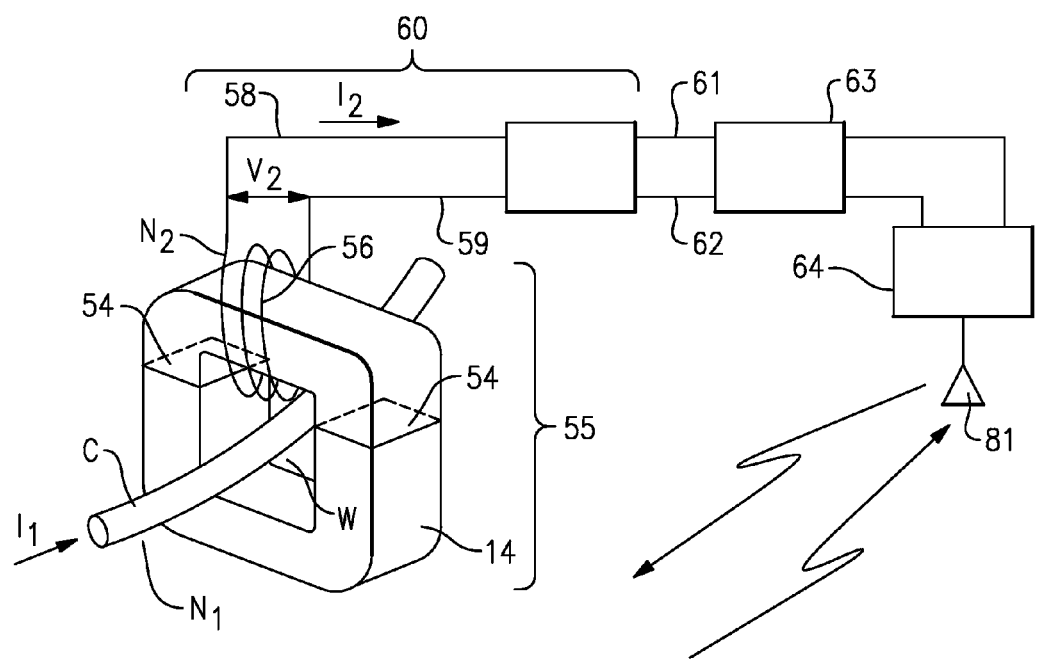
FIG. 9 illustrates a schematic view of the line mounted power supply, electronics and transmitter-receiver of the STR unit.

The transmitting and receiving antenna 81 for the on-board transmitter and receiver 64 shown in FIG. 9 is mounted on the housing 2. The antenna 81 is displayed in FIGS. 1 and 2 and is installed on the top left side in FIG. 1. The solar sensor assembly 134 is located at the top of this housing and on its vertical centerline (FIG. 13). The small hole 140 located directly to the right of the conductor 1 allows access and adjustment of the electric power line sag sensor 140 (FIG. 1).

Regardless of the overall conductor size all stranded conductors C are manufactured with the individual strand wires wrapped around a central strand in the form of a right hand or clockwise helix which has a helix angle $\alpha$ of 76°, as shown in FIG. 16. The stranding helix angle $\alpha$ of 76° is an important design feature of the conductor which will be utilized in developing a method of measuring the undisturbed surface conductor temperature.

Figure 16A:
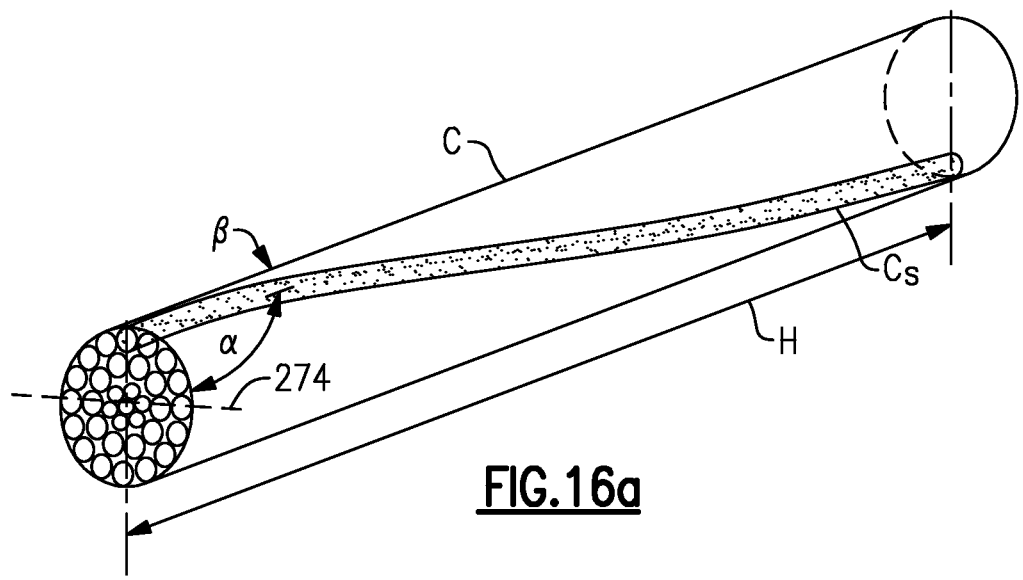
FIGS. 16a and 16b illustrate a stranded conductor formed by concentrically winding individual strands around a central strand.
Figure 16B:
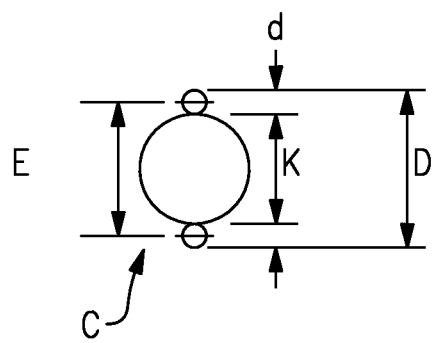

The conductor C as shown in the example of FIGS. 16a and 16b, includes a strand diameter d=0.175 inches with an overall conductor diameter of D=1.108 inches for a 795 kcmil 26/7 ACSR conductor, with a diameter under the first outside strand layer K=0.758 inches, $\alpha$=76 degrees, and $\beta$=14 degrees. With a pitch diameter E=0.933 inches, then the pitch P of the helix is defined as P=(tan $\alpha$)$\pi$E. Substituting E and $\alpha$ into this equation results in a pitch of the helix of 11.76 inches. In this example, H illustrates one half P with H=5.880. This means an individual strand makes one complete revolution around the conductor's central strand every 11.76 inches, and hence the angle, for example for the top strand, can be determined from a vertical reference line (clockwise) as the strand travels along the helix by knowing the axial distance from this reference line.

Figure 17:
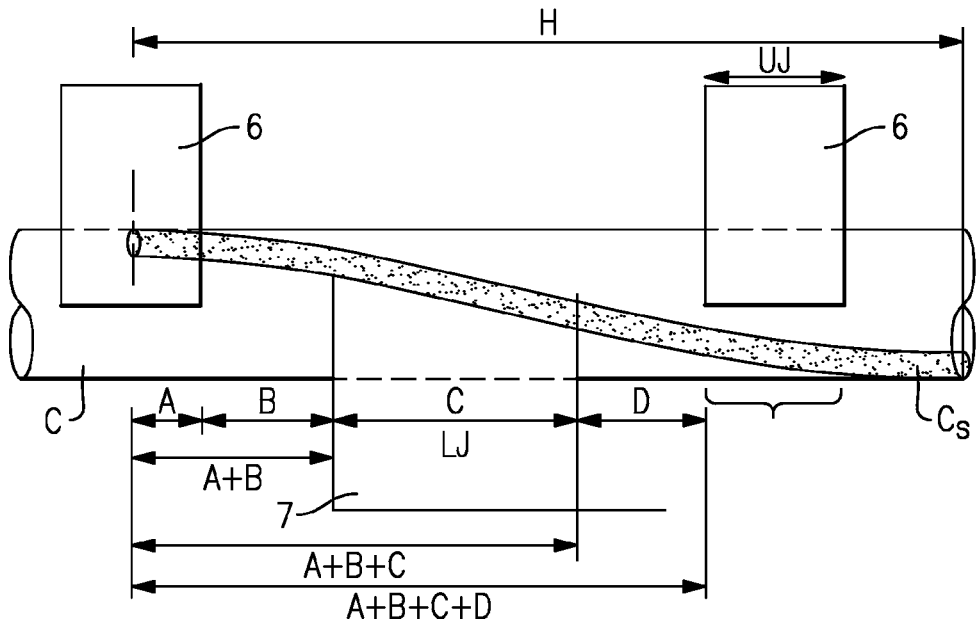
FIG. 17 illustrates a front view of upper jaws and a lower jaw.
Figure 18:
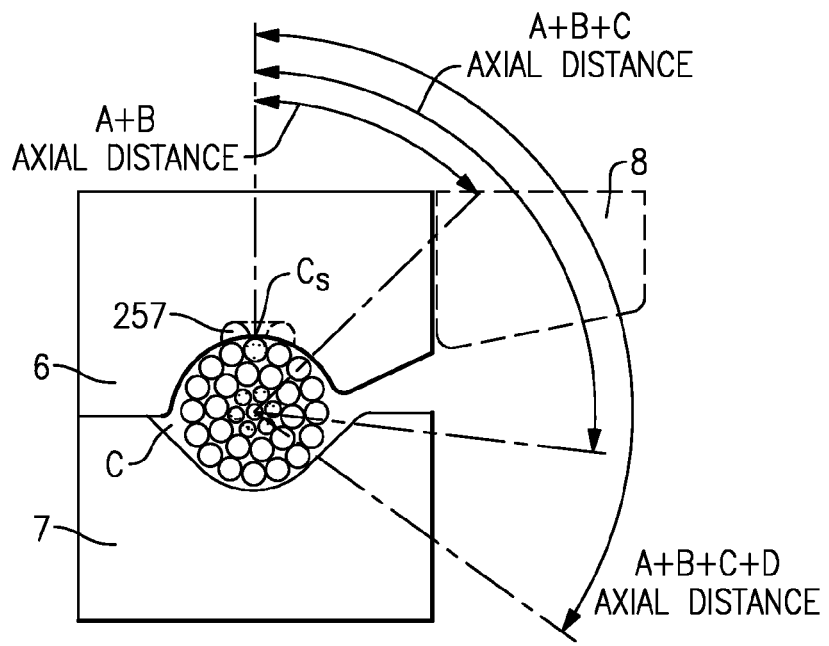
FIG. 18 illustrates a left side view of the upper jaws and the lower jaw.

As described earlier and shown in FIG. 17, the STR unit 1 includes two spaced apart upper jaws 6 and one lower jaw 7 placed between the upper jaws 6 and below the conductor C. FIG. 17 illustrates dimensions for the upper jaws 6, the lower jaw 7, and the conductor C according to one example embodiment. A shaded conductor strand Cs is shaded beginning at the top of the conductor C and under the left upper jaw 6. The upper jaws 6 have a thickness of UJ=1.00 inch, and the lower jaw 7 has a thickness of LJ=1.75 inches. The axial distance from the center of the left side upper jaw 6 to the inside edge is A=0.500 inches. The axial distance between the inside edge of the left upper jaw 6 and the left side edge of the lower jaw 7 is B=0.925 inches. The same is true for the axial distance measured from the right side edge of the lower jaw 7 to the left side edge of the right upper jaw 6, or B=0.925 inches. When the shaded strand Cs leaves the left upper jaw 6, the shaded strand Cs enters the open space between the left upper jaw 6 and lower jaw 7 and continues to be in open space as shown in FIG. 18 under the right upper jaw 6. Therefore, the lower jaw 7 and the right upper jaw 6 are never in contact with shaded strand Cs. If the shaded strand Cs is the strand being measured by the conductor temperature sensor then the only place where the shaded strand Cs could be in contact with the STR unit 1 is under the left side upper jaw 6.

Figure 19:
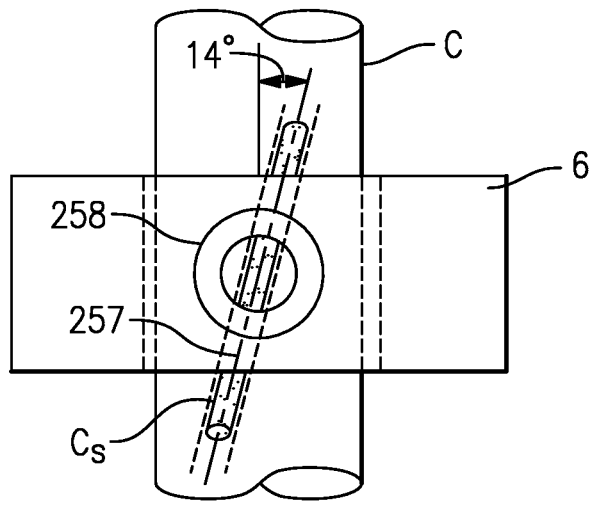
FIG. 19 illustrates a top view of the left upper jaw.

A semi-circular jaw slot 257 is located in the lower circular area of the upper jaws 6 as shown in FIG. 18 which is formed at an angle of 14° to match the angle the shaded strand Cs makes with the axial reference of the conductor C shown in FIG. 16. The top view of the jaw slot 257 is shown in FIG. 19. The jaw slot 257 has a width greater than the largest strand of any overall conductor diameter, so the upper jaws 6 are not in contact with the conductor strand being measured by the conductor temperature sensor of the conductor temperature sensor probe assembly 273 of FIG. 22.

As shown in FIG. 17, the shaded strand Cs being measured appears to come in contact with the lower jaw 7 near the right side of the lower jaw 7 but the shaded strand Cs does not contact the lower jaw 7.

As stated earlier, knowing the axial distance the strand travels on the helix defines the angular position of the strand as measured clockwise from the vertical reference shown in FIG. 16. As the shaded strand enters the area of the lower jaw 7 in this example, the axial distance traveled is A+B=1.425 inches, of which the angle at this point is 43.62° measured from the vertical reference line as shown in FIGS. 17 and 18. Therefore the shaded strand Cs is located in the open space above the lower jaw 7. As the shaded strand Cs travels further to the right it enters an open area formed in the right side of the lower jaw 7 as shown in FIG. 18. Specifically, at an axial distance of A+B+C=3.175 inches, where the shaded strand Cs could have the greatest contact on the right side edge of the lower jaw 7. However, the angle of the measured strand is now 97.19°, which is in the open area between the upper left jaw 6 and the lower jaw 7. Additionally, with an axial distance of A+B+C+D=4.100 inches with a measured angle of 125.51°, the shaded strand Cs is spaced from the upper jaw 6.

Figure 21:
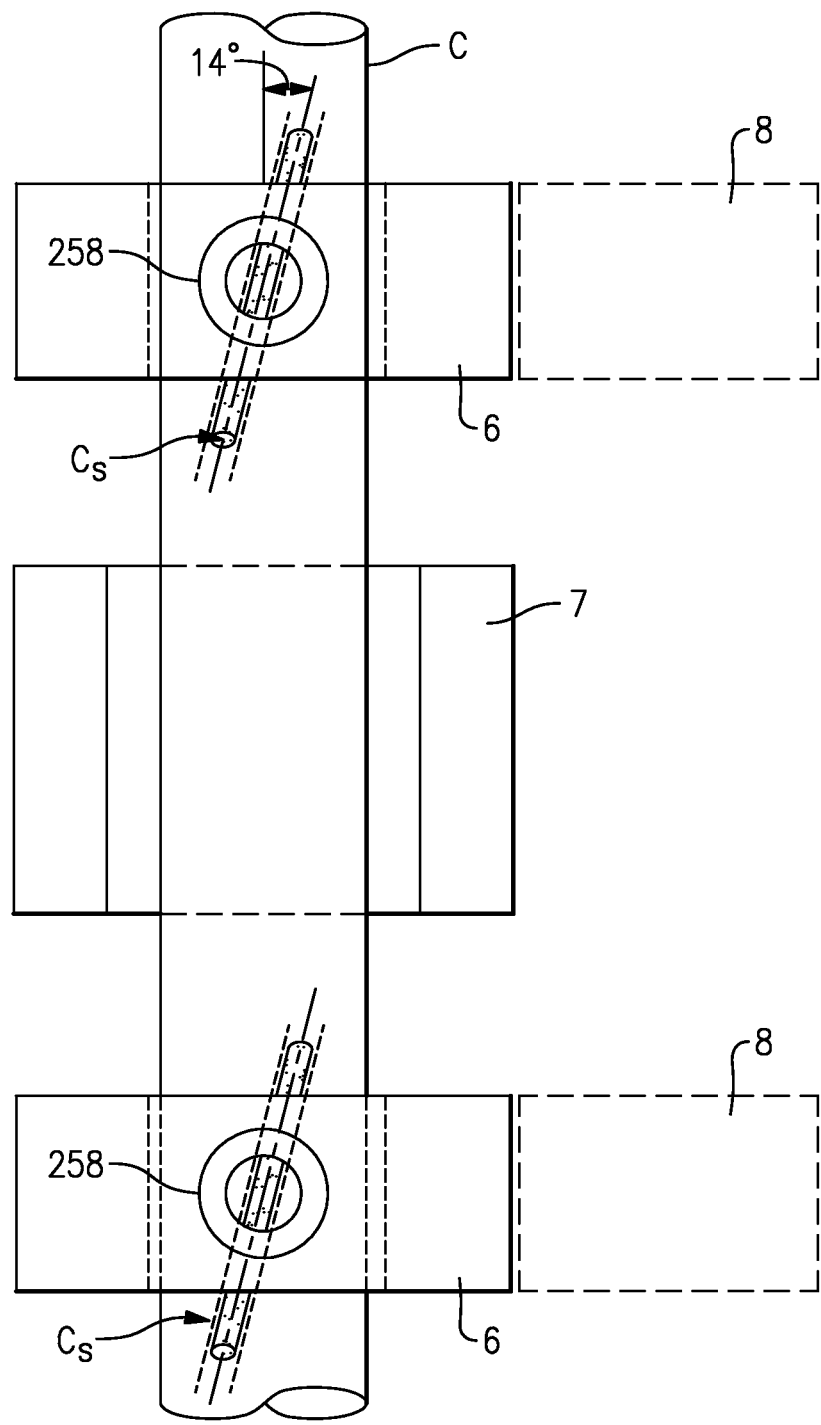
FIG. 21 illustrates a top view of the upper jaws and lower jaw.

If the conductor temperature of the shaded strand Cs is measured by the sensor placed in the upper left jaw 6, then there is no contact between the upper and lower jaws 6 and 7 and the conductor strand being measured, because of the spacing between the upper and lower jaws 6 and 7 being selected and the jaw slots 257 in the upper jaws 6. As shown in FIG. 21, the same is true if the conductor temperature sensor were measuring the top most strand of the conductor C in the upper right jaw 6. For this reason, two conductor temperature sensors may be installed, one in the left upper jaw 6 and one in the right upper jaw 6. Of course, the conductor temperature sensor probe assembly 273 could be placed at other angles with respect to the vertical reference and still measure the undisturbed temperature using the same concept.

If only one upper jaw 6 and one lower jaw 7 were used, then the upper jaw slot 257 which is cut at an angle within the surface of the radius of the upper jaw 6 would accomplish the same effect, and the same would be true if only the upper jaw were used. If four jaws were used in another example, that is two upper jaws 6 and two lower jaws 7 were employed in the design, then the application of jaw slots and spacing between jaws can also achieve no contact with the measured strand temperature. In general, the conductor temperature sensor is normally installed in the upper left jaw 6 as shown in FIG. 13, because if this sensor were installed in the right upper jaw 6 the measured conductor temperature could be affected by the heat generated by the coil winding 56 of the power supply transformer 55. The heat from the coil winding 56 is ejected through the vent and polarity mark 65 of FIG. 1 with the preferred location of the vent 65 being in the lower back of the curved portion of housing 2.

Another benefit of the conductor temperature measuring of the STR unit 1 is that there is negligible heat conduction between the strands of the conductor C which are in contact with the upper and lower jaws 6 and 7 because the oxide that forms on each of the strands of the conductor creates a thermal insulation between the strands and the heat conduction between the strands is very minimal. Therefore, there is a negligible effect of adjacent strand temperature on the measured strand. Test results have indicated that the conductor temperature of the measured strand as described above is within one percent (1%) of the measured conductor temperature of those strands remote from the STR unit 1 which are not disturbed or thermally affected by the installation of the STR unit 1 on the conductor C.

The conductor temperature sensor design described above employs a number of concepts which insures accurate measurement of the conductor temperature. First the two upper jaws 6 and the one lower jaw 7 allow the free flow of air around the conductor C. With the upper jaws 6 spaced apart axially along the conductor C with no mating jaw directly located below each upper jaw 6 allows the air to freely flow around the conductor C without materially effecting the forced and natural convection heat transfer from the conductor C. The lower jaw 7 is spaced between the upper two jaws 6 on the opposite side of the conductor C from the two upper jaws 6 and allows for air flow adjacent the conductor C.

Second, as shown in FIG. 1, when the two upper jaws 6 and the one lower jaw 7 are employed, the conductor C will have a slightly upward bending action after having been clamped onto the conductor C. This keeps the STR unit 1 from sliding on the conductor C even though the conductor C may be strung at a very steep angle when the conductor C traverses from one supportive structure to another; as with hilly terrain applications. Therefore, the STR unit 1 will always be measuring the conductor temperature at the desired location along the conductor C where the STR unit 1 is installed.

Third, the upper housing 2 of the STR unit 1 is open to the environment on all three sides, rather than having the housing encircling the conductor C as with other designs.

Finally, the two upper jaws 6, where the conductor temperature sensors could be mounted therein, are located at the far outer extremities of the upper housing 2 of the STR unit 1 rather than being located internal and between the two upper jaws 6. This insures the upper jaws 6 and the temperature sensor are nearest to the point of measurement of the undisturbed conductor temperature of the conductor C. The conductor temperature sensor probe assembly 273 of FIG. 22 installed within the upper jaws 6 could be applied to measure the temperature of any strand around the circumference of the surface of the conductor C, as long as a 14° jaw slot is located on the surface and at that location in the upper jaw 6 with no other upper or lower jaw 6 or 7 in contact with the measured strand. In another example, the temperature sensor could be installed in the bottom or lower jaw 7.

In another example, the temperature sensor probe assembly 273 could be located where neither of the upper and lower jaws 6 and 7 could conduct heat away from the strand being measured This could be for example in the open space between and around the upper and lower jaws 6 and 7.

Another desirable location to place the conductor temperature sensor probe is closest to the outside edge of the upper jaws 6 so it reads the undisturbed conductor C temperature and the sensor probe is physically protected from damage during installation of the STR unit 1.

Since the upper jaws and lower jaws 6 and 7 are removable to accommodate a wide range of conductor sizes, the conductor temperature sensor probe assembly 273 can be placed in the vertical location of the upper jaws 6 and near the outside edge. Since the wind which cools the conductor C due to forced convection can impinge at any angle with respect to the axis of the conductor C including parallel flow along the conductor C, it is necessary for the upper housing 2 to be as open as possible so as to not affect the temperature of the conductor C at the outer edge of the upper jaws 6.

Figure 20:
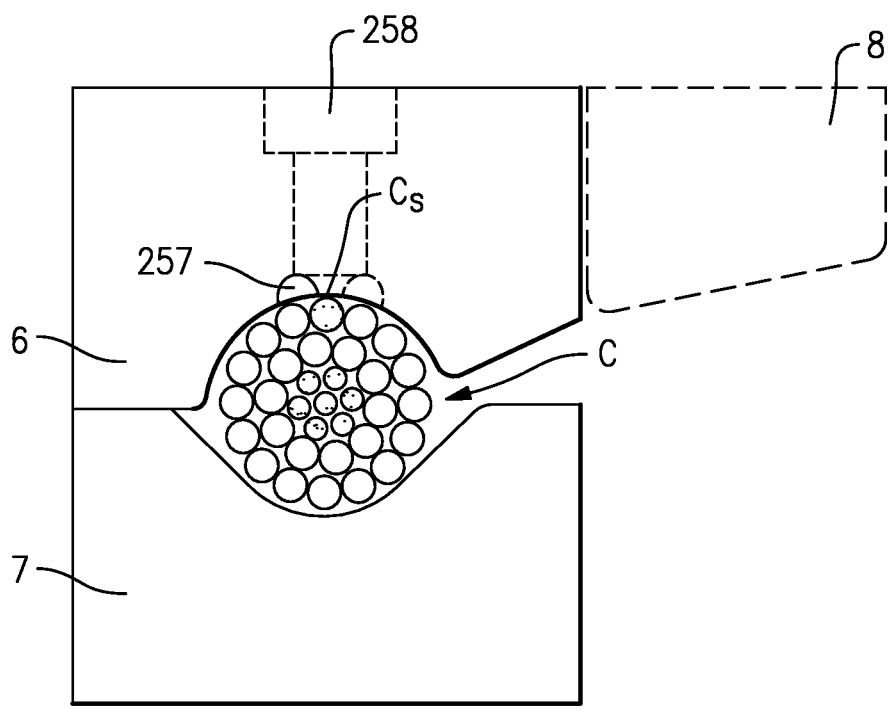
FIG. 20 illustrates a left side view of the upper left jaw and lower jaw.

As shown in FIG. 20, the upper jaws 6 include two elements. The first is the jaw insert 8 which is a permanent part and is not removed when the upper and lower jaws 6 and 7 are changed for a different range of conductor sizes. The slope of the inclined surface of the jaw insert 8 which first comes in contact with the conductor C upon installation of the STR unit 1 on the conductor C is smaller than the slope of the inclined surface of the front edge of the upper jaw 6. When the conductor C slides quickly down the inclined surface of the jaw insert 8 and comes in contact with the larger slope of the upper jaw 6, the conductor C jumps and falls into the circular portion of the upper jaw 6 without hitting the side of the temperature sensor probe assembly 273.

A conductor temperature sensor probe pocket 258 is shown in FIGS. 19-21. The pocket 258 is found in both of the upper jaws 6 in case two conductor temperature probes are employed. The pocket 258 includes a first large diameter hole at the top of the upper jaw 6 and a second smaller diameter hole located directly below the large diameter hole. The smaller diameter hole extends through the upper jaw 6. The purpose of the pocket 258 is to provide access to the conductor temperature probe to the top upper most strand of the conductor C and to protect the probe from being damaged when the STR unit 1 is installed on the conductor C. There is also clearance between the probe and the inside wall of the pocket to prevent heat conduction from the probe to the wall.

According to an on the right side edge example embodiment of the conductor temperature sensor probe 273, the conductor temperature sensor probe 273 must be adjustable to measure accurately the conductor temperatures of the smallest conductor C which is only 0.162 inches in diameter and up to 1.165 inches which is the largest diameter conductor C encountered on distribution electric power lines.

FIGS. 22-26 illustrate the temperature sensor probe assembly 273. As shown in FIG. 23, the temperature sensor probe assembly 273 includes an electrically conductive and magnetically shielded protection tube 169 and a conductor temperature sensor 172 with leads 173 and 174. The conductor temperature sensor 172 is mounted at the bottom and inside the protection tube 169 with a thermally conductive material 259. Isolation slots 261 and 262 are cut in the side walls of the protection tube 169 which prevent heat from being conducted from the conductor C up the protection tube 169. The leads 173 and 174 are connected to the conductor temperature sensor 172 and are twisted to prevent magnetic field interference with the output of the conductor temperature sensor 172.

Figure 28:
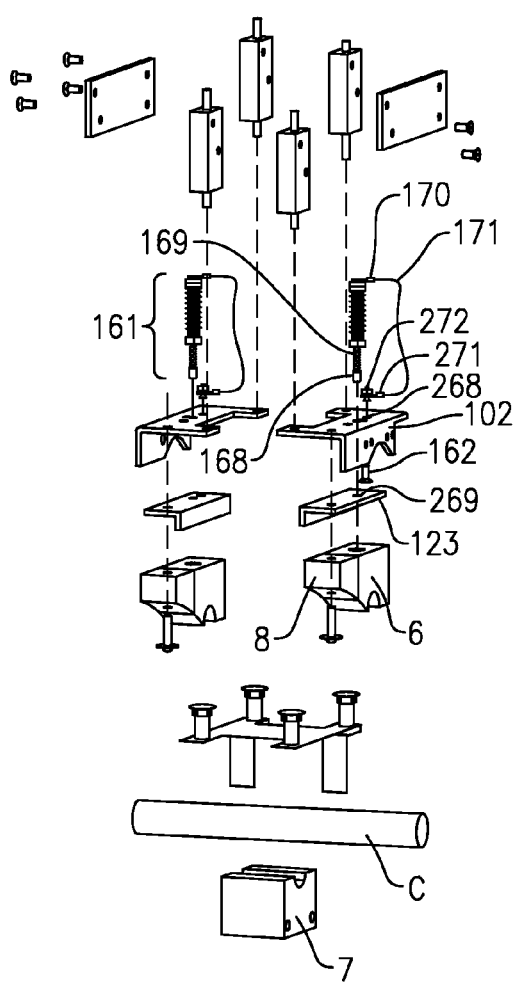
FIG. 28 illustrates an exploded view of an example virtual grounding device and the temperature sensor.

A flared top 260 of the protection tube 169 is not made until after the assembly shown in FIG. 24 is completed. First an electrically conductive and thermally conductive shoe 168 is installed on the bottom of the protection tube 169. Second, a thermally insulated isolation washer 263 is slid over the protection tube 169 from the top and seats on top of the shoe 168. The purpose of the washer 263 is to prevent heat from being conducted from the shoe 168 to a compression spring 264. Third, the compression spring 264 is placed over the protection tube 169 and seats on top of the isolation washer 263. Fourth, a threaded nipple 265 is slid over the protection tube 169 and seats on top of the compression spring 264. Fifth, a ring connector 170 is placed over the protection tube 169 and the top of the protection tube 169 is flared over the ring connector 170. Sixth, the conductor temperature sensor 172 with the leads 173 and 174 attached thereto is pushed inside and to the bottom of the protection tube 169 and is cemented with a thermally conductive material 259 as shown in FIG. 27. With the assembly of FIG. 22 now complete, the shoe 168, the protection tube 169, and the ring connector 170 can be pushed up with a force which is equal to the downward force applied by the compression spring 264. Seventh, the assembly of FIG. 24 is now ready to have two locking ring nuts 266 threaded to the top of the threaded nipple 265 as shown in FIG. 22. A larger adjustment spring 267 is slid over the bottom of the threaded nipple 265 and seats on the underneath side of the two locking ring nuts 266. Eighth, the ground lead 171 shown in FIG. 22 is compressed onto the ring connector 170, and the threaded nipple 265 is placed through the hole 268 in the upper jaw holder 102 and through the hole 269 in the jaw keeper 123 as shown in FIG. 22 and in the exploded view of FIG. 28. Ninth, the ring nut 270 is placed over the shoe 168, the compression spring 264 and is threaded onto the lower portion of the threaded nipple 265.

Figure 29:
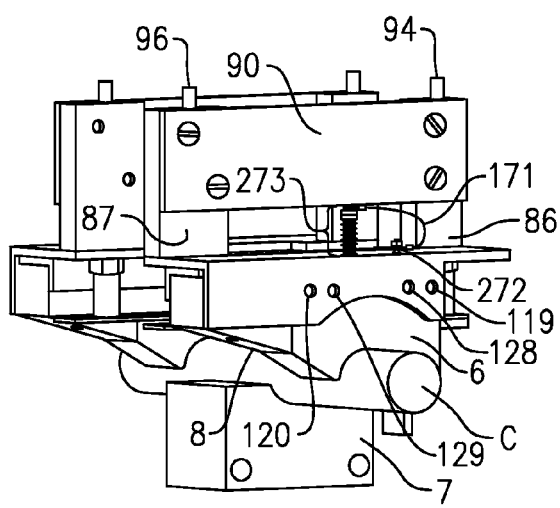
FIG. 29 illustrates a collapsed view of the virtual grounding device and the temperature sensor mounted on the conductor.

By turning the ring nut 270 clockwise, the temperature sensor probe assembly 273 including the shoe 168 can be adjusted downward and if the ring nut 270 is turned counter-clockwise, the temperature sensor probe assembly 273 will be adjusted upward. Of course, this adjustment is accomplished with the upper jaw 6 removed in order to gain access to the ring nut 270. Tenth, the ground lead 171 includes another ring connector 271 which is compressed on the other end of the ground lead which is attached to the case ground screw 162 of FIGS. 22 and 28 and is held tight against the upper jaw holder 102 with a nut 272. Since this upper jaw holder 102 is attached to the upper housing 2, then when the shoe 168 is in contact with the conductor C the upper and lower housings 2 and 3 are at the same voltage as the conductor C, and the conductor temperature sensor probe assembly 273 also measures the surface temperature of the conductor C. The installed conductor temperature sensor probe assembly 273 is shown in FIG. 29.

Figure 30:
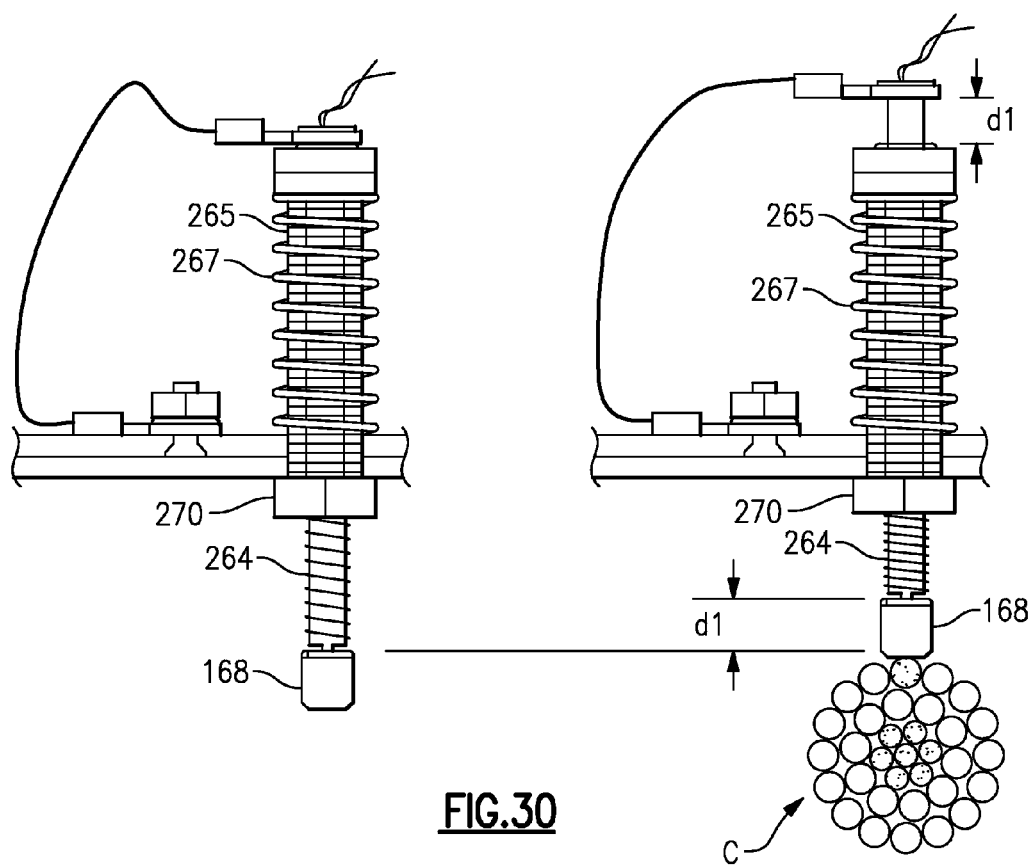
FIG. 30 illustrates the adjustment of the temperature sensor probe assembly for a large conductor and the associated compression of the temperature sensor probe before and after installation on a large conductor.

The adjustment shown in FIG. 22 is for the largest conductor size of 1.165 inches in diameter prior to the installation on the largest conductor C. FIG. 30 illustrates the compression spring 264 in an uncompressed position on the left and on the right illustrates the compression spring 264 being compressed after the conductor temperature sensor probe assembly 273 contacts the conductor C. Note the ring nut 270 is at its lowest position on the threaded nipple 265. Here the compression spring 264 is compressed up d1=0.25 inches.

Figure 31:
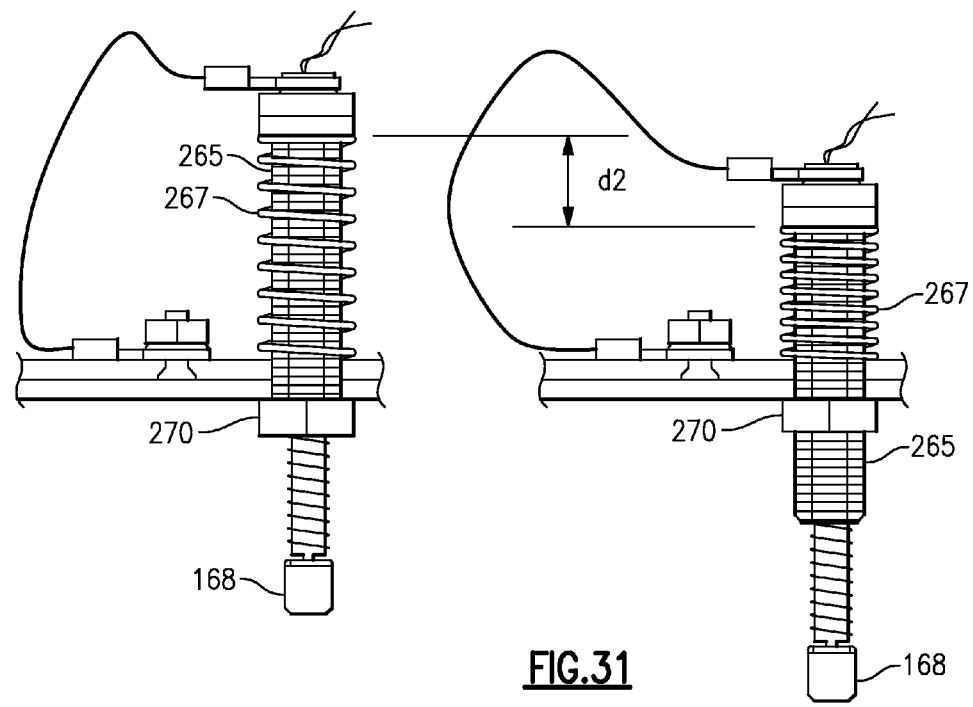
FIG. 31 illustrates an adjustment of the conductor temperature sensor probe assembly for a small conductor prior to installation on the small conductor.
Figure 32:
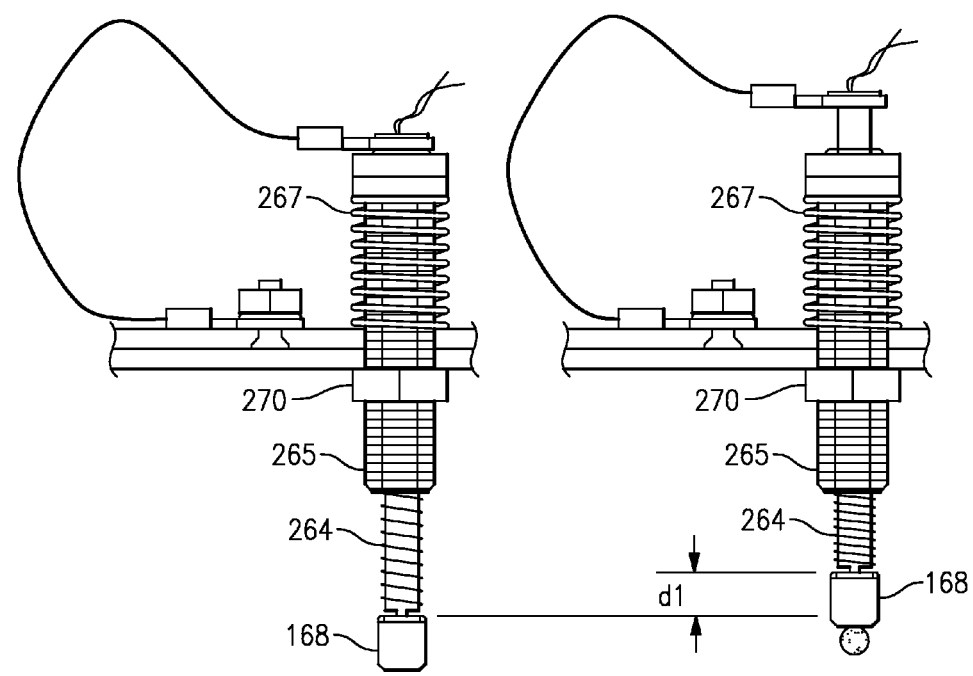
FIG. 32 illustrates an adjustment of the conductor temperature sensor probe assembly for the small conductor and the associated compression of the conductor temperature sensor probe assembly after installation on a small conductor.

Referring to FIG. 31, the temperature sensor probe assembly 273 on the right illustrates the ring nut 270 adjusted to its highest position on the threaded nipple 265 prior to the installation on the smallest conductor C. Notice the adjustment spring 267 has been compressed down d2=0.50 inches from the reference level shown on the temperature sensor probe assembly on the left. The compression of 0.50 inches results in the difference between the largest diameter conductor radius and the smallest diameter conductor radius or 1.165/2−0.162/2=0.50 inches. FIG. 32 illustrates that the compression of the compression spring 264 for the smallest conductor size of 0.162 inches is the same value of d1=0.25 inches as for the largest conductor C of FIG. 30. Having the same compression distance regardless of the conductor size allows the same contact pressure of the shoe 168 for all diameter sizes of conductors C within the full range of 0.162 inches to 1.165 inches. The measured conductor temperature is a function of the contact pressure and the higher the pressure the higher the temperature reading up to a limit. Having a constant contact pressure throughout all diameter conductor sizes within the range insures accurate measurements of the conductor temperature.

As discussed earlier, and shown in FIGS. 19-21, the pocket 258 is formed in the upper jaws 6 to provide access for the temperature sensor probe assembly 273 to the conductor C. Furthermore, the pocket 258 provides clearance between the temperature sensor probe assembly 273 and the inside wall of the pocket 258. This insures negligible heat conduction transfer between the shoe 168 and the upper jaws 6 and allows the ring nut 270 not to contact the upper jaws 6. The threaded nipple 265 can also be adjusted up or down inside the pocket 258 of the upper jaws 6.

Figure 33:
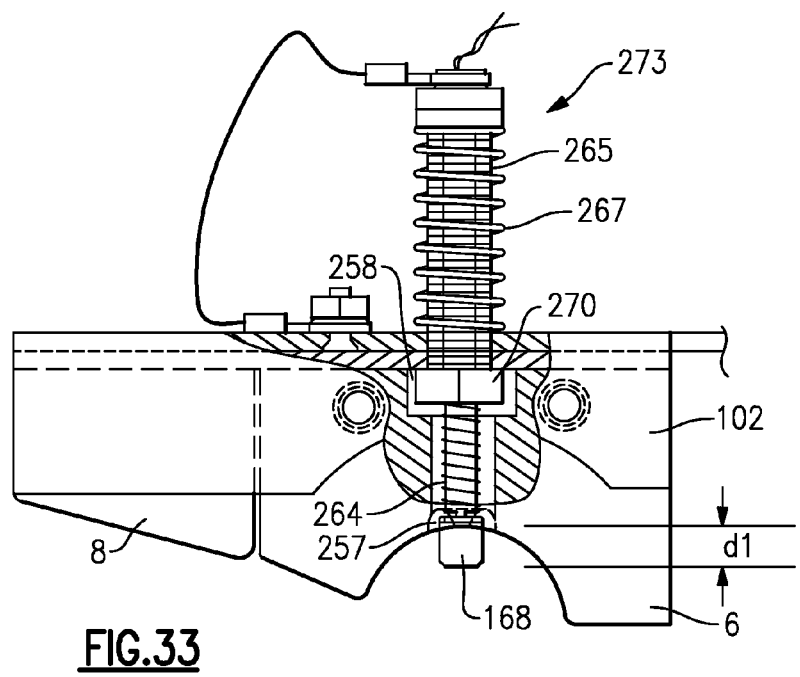
FIG. 33 illustrates the conductor temperature sensor probe assembly and adjustment before installation on the largest conductor in range 4.

FIG. 33 illustrates a cut away view of the installation of the temperature sensor probe assembly 273 in the upper right side jaw 6. The ring nut 270 has already been adjusted as in FIG. 22 for the largest diameter conductor of 1.165 inches. The bottom end of the shoe 168 extends down d1=0.250 inches below the surface of the upper radius of the largest diameter conductor formed in the upper right side jaw 6.

Figure 34:
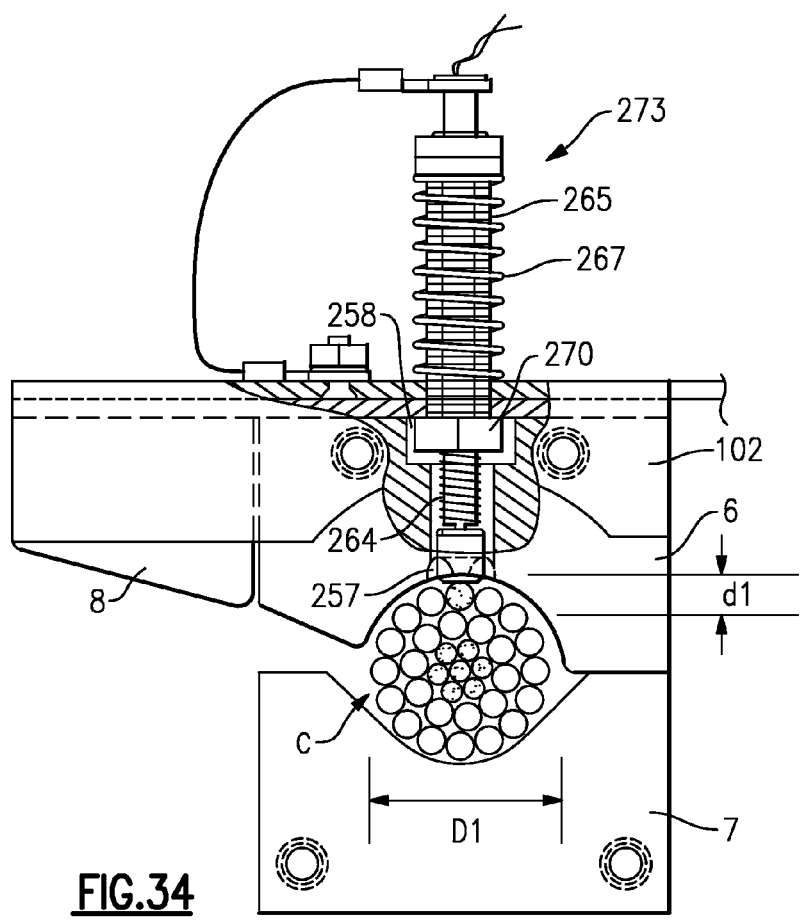
FIG. 34 illustrates the conductor temperature sensor probe assembly and upper and lower jaws after installation on the largest conductor in range 4.

FIG. 34 illustrates how the compression spring 264 is depressed d1=0.250 inches when installed on the largest conductor C diameter of D1=1.165 inches. Notice the shoe 168 is directly on top of the upper most strand of the conductor C and is totally isolated from the interior wall of the pocket 258, and the jaw slot 257 cut at 14° in the bottom of the right side upper jaw 6 prevents the upper jaw 6 from coming in contact with the upper most strand of the conductor C.

FIGS. 33-34 are configured for conductors in size range 4, which is the largest diameter conductor range. There are five ranges of upper and lower jaw 6 and 7 sizes which allow the STR unit 1 to be installed on hundreds of conductor size diameters ranging from the smallest of 0.162 inches to the largest of 1.165 inches. These five ranges are defined as Range 0, Range 1, Range 2, Range 3, and Range 4.

Figure 35:
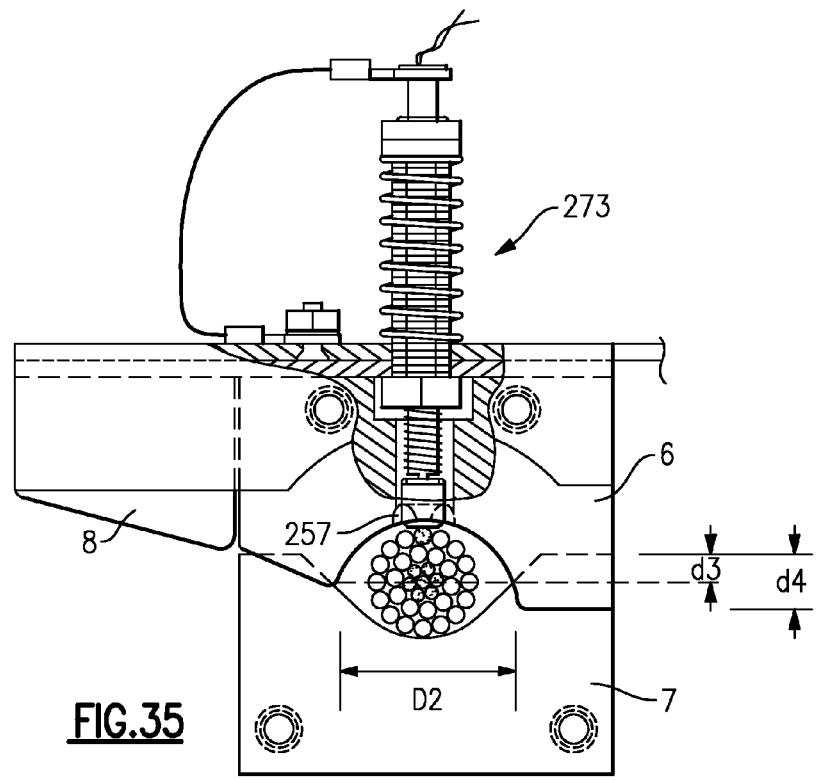
FIG. 35 illustrates the conductor temperature sensor probe assembly and the upper jaw and the lower jaw after installation on the smallest conductor in range 4.

The smallest conductor size in Range 4 is shown in FIG. 35 for the same set of upper and lower jaws 6 and 7 that were used for the largest diameter conductor of 1.165 inches. Notice the lower jaw 7 has now moved up d3=0.1747 inches from the reference position for the largest diameter conductor C to a higher position for the smallest diameter conductor of D2=0.918 inches. The reason why the change in the height of the lower jaw 7 is not only the change in the diameters between the largest and smallest conductors or D2-D1, which is 0.247 inches (1.165−0.918=0.247 inches), but is also because the smaller conductor C fits lower in the lower jaw 7 by a distance of d3=0.1747 inches. Therefore, the total distance the lower jaw 7 moves up for the smallest conductor is the sum of the change in diameters or 0.247 inches plus the change in the position of the smaller conductor down in the lower jaw of 0.1747 inches, or d4=0.4217 inches.

Not only does the design of the temperature sensor probe assembly 273 insure a constant pressure of the shoe 168 on the conductor C throughout all the different diameter conductors C but the jaw design insures the conductor C is nearly in the center on a vertical centerline of the "C" loop coils 156 and 157 even though the STR unit 1 is installed on the full range of the largest and smallest conductor sizes. The horizontal centerline 274 (FIG. 16) of all the largest conductors C of each Range can be offset up 0.350 inches from the horizontal centerline of the "C" loop coils 156 and 157. The offset for the largest conductor in each Range is a constant value of 0.350 inches, but for the smaller conductor sizes in each Range the offset is somewhat higher with the greatest offset up from the horizontal centerline of the "C" loop coils being 0.474 inches. The offsets for the largest and smallest conductor in each range are as follows: 1) Range 0: 0.350 to 0.398 inches; 2) Range 1: 0.350 to 0.424 inches; 3) Range 2: 0.350 to 0.439 inches; 4) Range 3: 0.350 to 0.403 inches; and 5) 0.350 to 0.474 inches.

With the uncalibrated error of the "C" loop coils 156 and 157 in the presence of the power supply transformer 55 and with the "C" loop coils 156 and 157 being moved up or down ±0.75 inches on the vertical centerline, there was only a 0.989% measure error, even though the conductor diameter size ranged from 1.00 inch to 3.50 inches. The offsets for each conductor range above are well below the test offset values of ±0.75 inches.

Figure 36:
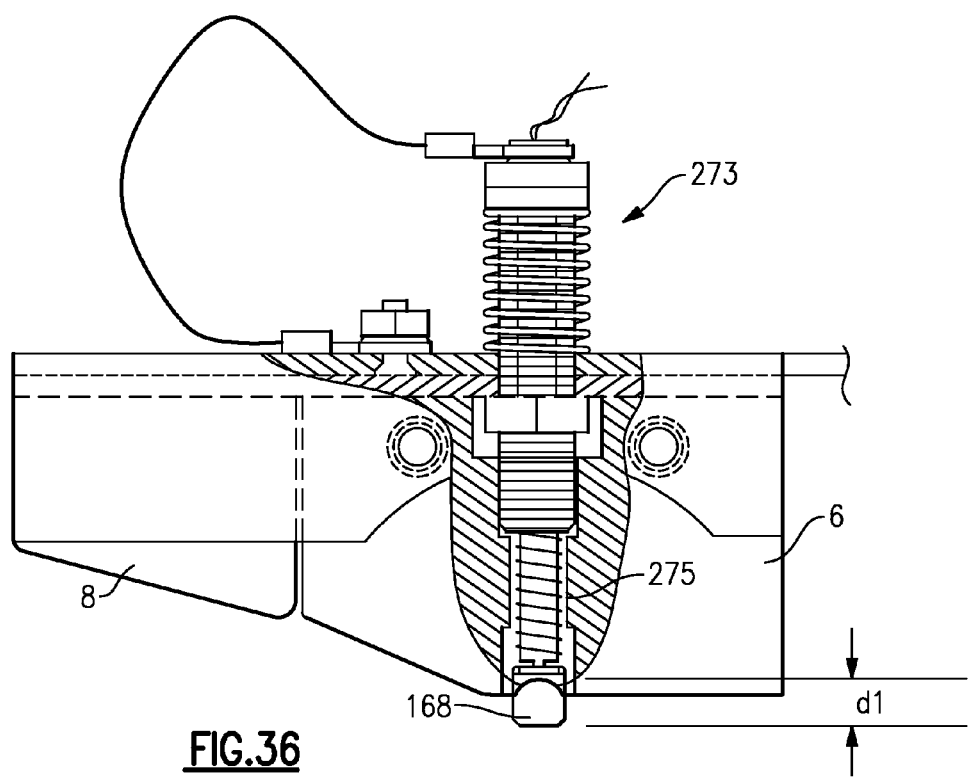
FIG. 36 illustrates the conductor temperature sensor probe assembly before installation on the largest conductor size in range 0.
Figure 37:
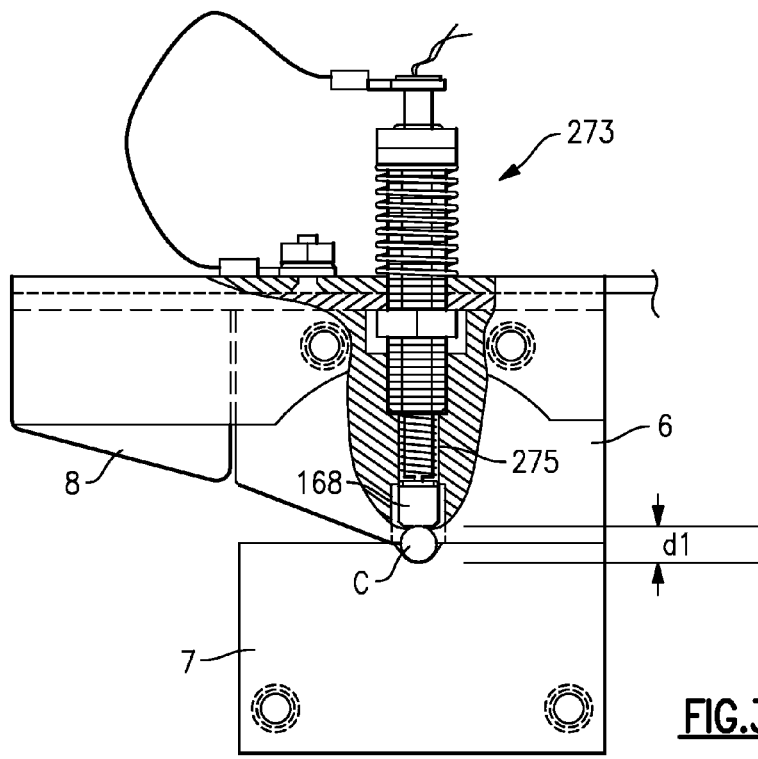
FIG. 37 illustrates the conductor temperature sensor probe assembly and upper and lower jaws after installation on the largest conductor size in range 0.
Figure 38:
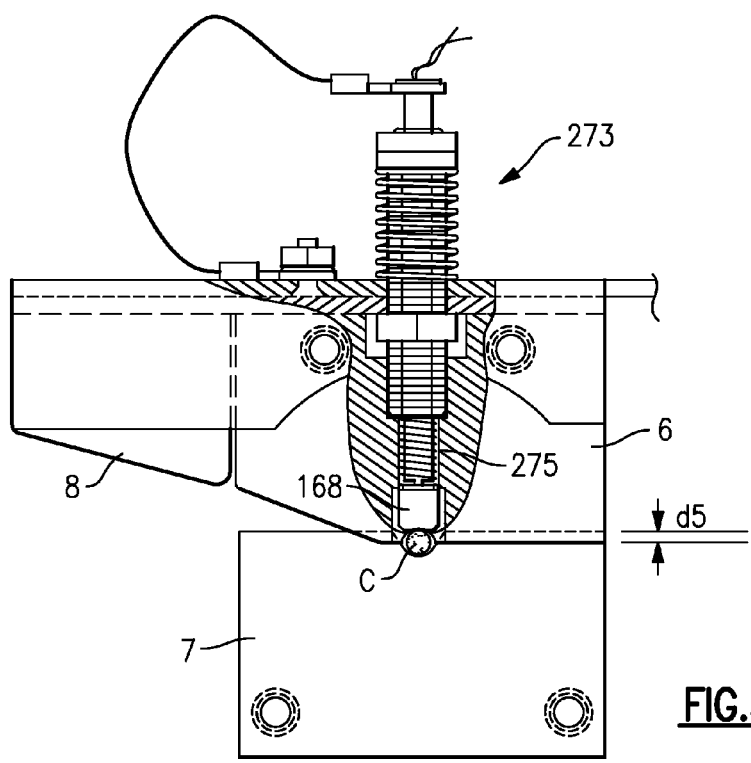
FIG. 38 illustrates the conductor temperature sensor probe assembly and upper and lower jaws after installation on the smallest conductor in range 0.

FIG. 36 illustrates the position of the temperature sensor probe assembly 273 before installation on the largest conductor C in Range 0. In this case, the largest size diameter conductor is a #2 AWG copper with a diameter of 0.2576 inches. Here again as before, the shoe 168 extends down d1=0.250 inches below the top curvature of the circular form of the upper jaw 6. When the STR unit 1 is installed on the conductor C, as in FIG. 37, the shoe 168 is depressed 0.250 inches and the same contact pressure on the conductor C is achieved as was the case for the largest and smallest diameter conductors in Range 4. However, in this case, there is a major difference in the upper jaw 6 design in that there is no 14 degree slot 257, because there is only one strand of the conductor C. When the same set of jaws in Range 0 are applied to the smallest size diameter conductor of 0.162 inches for the #6 AWG copper, the shoe 168 is depressed d1=0.25 inches, but the lower jaw 7 moves up not only d5=0.0676 inches, but an additional 0.0956 inches higher than for the #2 AWG copper conductor C. Again this change in upward movement of the lower jaw 7 is not only due to the difference in the conductor diameters or 0.2576−0.162=0.0956 inches, but also due to the smaller conductor fitting lower in the lower jaw by a distance of 0.0676 inches as shown in FIG. 38. Therefore, the total distance the lower jaw 7 moves from its position with the largest conductor is 0.0956 inches plus 0.0676 inches or 0.1632 inches. Although examples of the other Ranges 1, 2, and 3 will not be described, the same procedure follows as with Range 0 and Range 4. The range of conductor size diameters for Range 1 is 0.316 inches for the #2 ACSR 6/1 stranding to 0.464 inches for the 3/0 aluminum 7 strand; Range 2 is 0.502 inches for the 3/0 ACSR 6/1 stranding to 0.679 inches for the 350 kc mil aluminum 19 strand; and Range 3 is 0.813 inches for the 500 kcmil copper 37 strand, to 0.918 inches for the 636 kcmil aluminum 37 strand.

The design of the upper jaws 6 and the lower jaw 7 are constructed to insure the conductor C remains nearly in the center and always on the vertical centerline of the "C" loop coils 156 and 157 no matter what size conductor the STR unit 1 is installed upon within the range of the conductor size diameters from 0.162 inches to 1.165 inches.

The two upper jaws 6 are based on the same design concepts for all the Ranges 0 through 4. These design concepts are as follows: (1) The diameter of the hole in the upper jaws 6 adjacent to the upper most part of the conductor C is always based on the largest size conductor diameter within a specific range; (2) With the aid of FIG. 39, the horizontal centerline 274 of the largest conductor C within a specific range is always laid out at the bottom of the upper jaw 6; (3) The height, width and thickness of all upper jaws 6 are the same; (4) The centerline of the pocket 258 is always located on the vertical centerline of the "C" loop coils 156 and 157, as well as the vertical centerline of the largest conductor C; and (5) The jaw slot 257 is milled at an angle of 14 degrees to coincide with the helix angle of the stranded conductor C and with a diameter greater than the largest strand diameter of any conductor C within all ranges.

Figure 39:
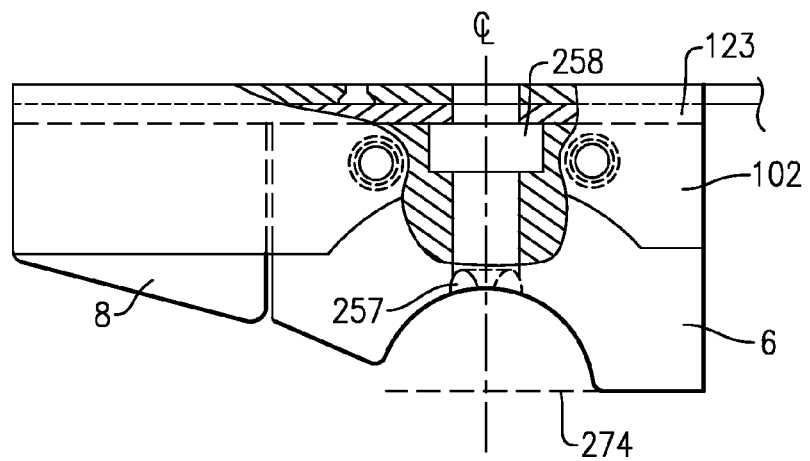
FIG. 39 illustrates a right side view of the upper jaw for the range 4 conductor.
Figures 40, 41:
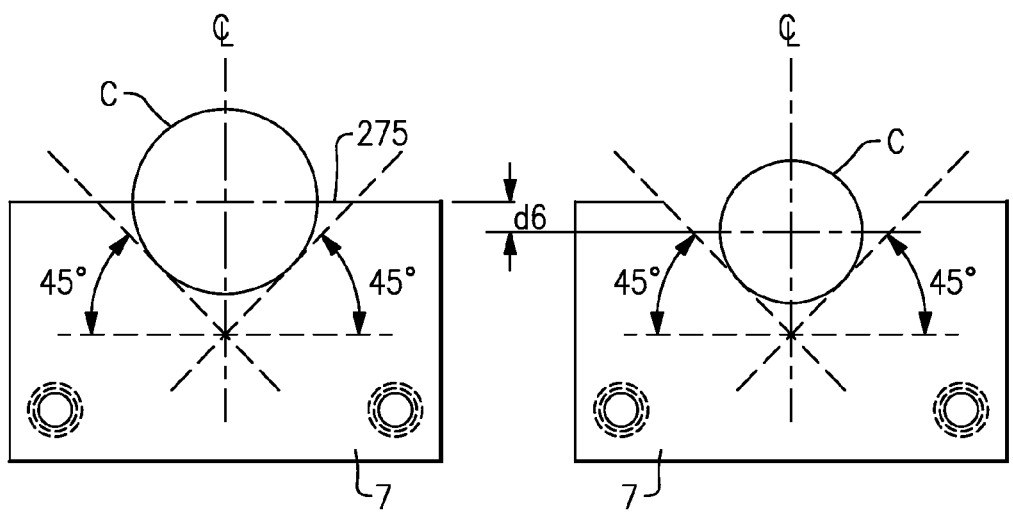
FIG. 40 illustrates the lower jaw for the largest conductor size in range 4.
FIG. 41 illustrates the lower jaw for the smallest conductor size in range 4.

The lower jaw 7 design concepts of FIGS. 40 and 41 are as follows: (1) The largest size conductor diameter within a specific range is laid out with its horizontal centerline 275 located at the top of the lower jaw 7; (2) Tangent lines at an angle of 45 degrees to the horizontal are constructed on each side of the largest conductor C within a specific range of sizes with the tangent lines intersecting below and on the vertical centerline of the conductor C and the lower jaw 7; (3) The lower jaw 7 width, height and thickness are the same for all ranges; (4) Referring to FIG. 41, the smallest size conductor diameter within this same specific range is placed on the vertical centerline of the lower jaw 7 and dropped down until it contacts the 45 degree tangent lines constructed for the largest size conductor within the same specific range; (5) An arc with a radius equal to the radius of the smallest conductor size is constructed on the vertical centerline of the lower jaw 7 which connects to the tangents of the 45 degree slope lines of the largest size conductor C in the same specific range. Although the example given for designing the upper jaws 6 and lower jaw 7 of FIGS. 39-41 is for the Range 4, this same process is repeated for the other Ranges 0, 1, 2, and 3. In FIG. 41 the horizontal centerline of the smallest conductor C is d6=0.1747 inches below the horizontal centerline for the largest conductor C. Because the smaller conductor C is positioned lower in the lower jaw 7 then the lower jaw 7 will have to be raised 0.1747 inches higher than the largest conductor plus the change in diameter between the smallest and largest conductor C before it comes in contact with the upper jaw 6 in FIG. 39. This explains why the change in height in the lower jaw of 0.1747 inches is greater than the change in diameters between the largest and smallest size conductors of which in Range 4 is 0.247 inches.

Figure 42:
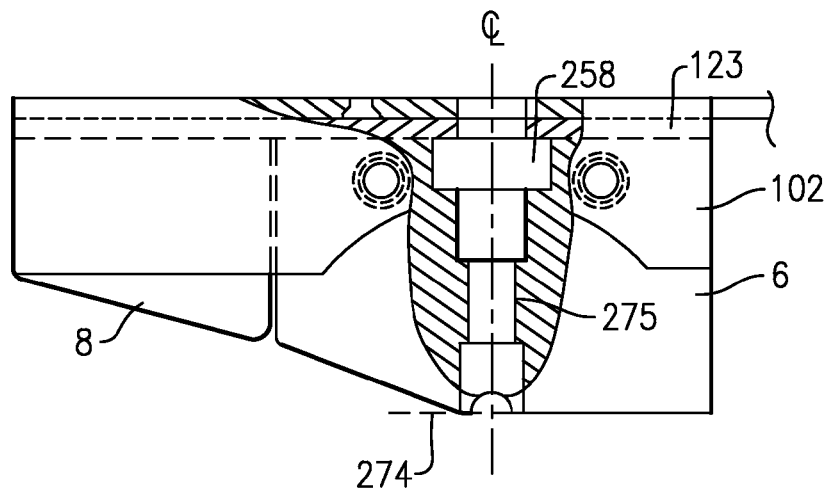
FIG. 42 illustrates a right side view of the upper jaw design for a range 0 conductor.
Figures 43, 44:
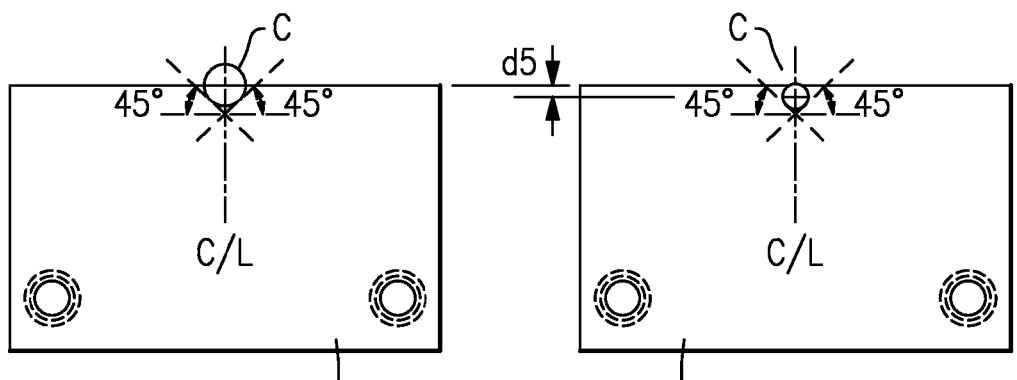
FIG. 43 illustrates the lower jaw for the largest conductor size in range 0.
FIG. 44 illustrates the lower jaw for the smallest conductor size in range 0.

Even though the design concepts are the same for all Ranges 0 through 4, only Range 0 is shown in FIGS. 42-44. FIG. 42 illustrates the horizontal centerline of the largest conductor size in Range 0 is located at the bottom of the upper jaw 6 and is aligned with the horizontal centerline 274. Because the height of the pocket 258 is much longer for the Range 0 upper jaw 6 than shown in FIG. 42 for the Range 4 upper jaw 6, a constricted area 275 provides extra lateral support for the temperature sensor probe assembly 273 as also shown in FIGS. 36-37.

When the lower jaw 7 is moved upward and comes in contact with the underneath side of the conductor C and is tightened onto the conductor C, the lower jaw 7 now causes the conductor to become clamped between the upper two jaws 6 and the lower jaw 7. As discussed in FIG. 6 the lower magnetic core 14 is pushed upward after the lower core 14 comes in contact with the upper core 40 and causes the large compression springs 41, which are pushing down on the upper magnetic core 40, to become compressed. Because of the design of the upper and lower jaws 6 and 7 discussed above, the distance the compression springs 41 are compressed is the same for the largest size conductor C in each of the Ranges 0 through 4. This is an important additional design concept, because the magnetic repulsion force, due to the current flowing in the conductor C, between the upper magnetic core 40 and the lower magnetic core 14 becomes nearly constant once the flux becomes saturated at the higher current levels flowing in the conductor C. Therefore, the compression springs 41 are designed to have a greater compressive force than the highest repulsive force between the upper and lower magnetic cores 14 and 40 when the upper and lower magnetic cores 14 and 40 become saturated, because the distance they are compressed for the largest size diameter conductor in each Range 0 through 4 is the same. There is however an increase in compressive force applied by the compression springs 41 for each of the smallest conductors within each range, since, for example in Range 4, the lower jaw 7 moves up an additional 0.4217 inches more than for the largest conductor as shown in FIGS. 40 and 41. As already demonstrated for Range 0, the lower jaw 7 moves up an additional 0.0676 inches plus the change in diameters of 0.0956 inches for the smallest conductor in this Range. This displacement of 0.0676 inches as shown in FIGS. 43 and 44.

Several exemplary features of the temperature sensor probe 273 and the upper and lower jaws 6 and 7 are as follows: (1) The adjustable temperature sensor probe assembly 273 maintains the same contact pressure between the shoe 168 and the upper most strand of the stranded conductor C thereby insuring accurate temperature measurements for all the conductors C throughout the entire range of conductor diameters; (2) The jaw slot 257 in the upper jaws 6 is milled at an angle of 14 degrees on the surface of the upper jaws 6 adjacent to the upper part of the conductor C which matches the helix angle of 14 degrees for the stranding in the conductor C, thus resulting in no contact between the upper and lower jaws 6 and 7 with the upper most strand of the conductor C being measured by the temperature probe; (3) The isolation slots 261 and 262 cut on each side of the protection tube 169 and above the shoe 168 and the isolation washer 263 located between the top of the shoe 168 and the bottom of the small compression spring 264 impede heat from being conducted from the shoe 168 up the temperature sensor probe assembly 273; (4) The set of only five upper and lower jaws 6 and 7 span the entire range of conductor diameter sizes and maintain a constant offset upward from the horizontal centerline of the "C" loop coils 156 and 157 of only 0.350 inches for the largest size conductor of each Range. In addition, for the smallest conductor size within each Range includes a maximum offset up from the horizontal centerline of the "C" loop coils 156 and 157 of only 0.474 inches which is less than the +0.75 inches of the offset that maintains accuracy of current measurements of less than one percent. (5) The set of five upper and lower jaws 6 and 7 jaw size Ranges insure the compression springs 41 provide a compressive force greater than repulsive force on the magnetic cores of the power supply module 63 for the largest and smallest conductors C in each of the five Ranges.

Figure 45:
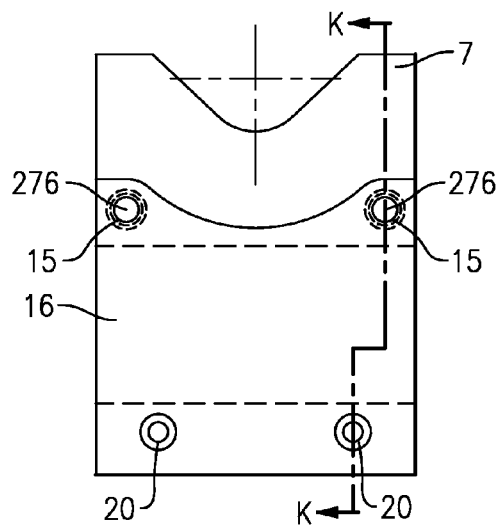
FIG. 45 illustrates a right side view of a lower snap-in jaw for range 4.
Figure 46:
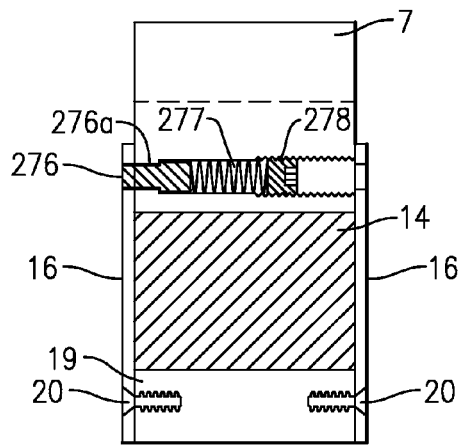
FIG. 46 illustrates a sectional view taken along line K-K of FIG. 45.

Five jaw sets can accommodate Range 0 through Range 4 conductors C when clamping the STR unit 1 onto the conductor C. A method of changing the two upper jaws 6 and the lower jaw 7 on the STR unit 1 is illustrated in FIGS. 45 and 46 for the lower jaw 7 of Range 4. As discussed in FIG. 3, the lower jaw holder 16 has two holes 15 at the top which intercept the lower jaw 7 and two holes 20 at the bottom of which screws are threaded into the bottom block 19. The jaw holders 16 are shown in Section K-K of FIG. 45. One of the jaw holders 16 is placed on the right side of the lower core 14 and the other jaw holder 16 is placed on the left side of the lower magnetic core 14.

Two holes 276*a* are drilled in the lower portion of the lower jaw 7. The two holes have a reduced diameter on the left side as shown in FIG. 46 and a larger diameter extending from the reduced diameter to the right side of the lower jaw 7. A portion of the larger diameter on the right side is threaded which allows a set screw to be threaded therein.

A pin 276 including a portion with a larger diameter and a portion with a reduced diameter portion is inserted into each of the two holes 276*a*. The pin 276 stops when the larger diameter portion of the pin 276 seats up against the smaller diameter hole 276*a* as shown in FIG. 46. The reduced diameter portion of the pin 276 extends through the holes 15 and is flush with the outside surface of the left side lower jaw holder 16. A small compression spring 277 is placed in each of the two holes 276*a* and is slightly compressed with a threaded set screw 278. The two spring pins 276 do not have a vertical force placed on them, because the magnetic core 14 is located directly below the lower jaw 7 which is backed up with the bottom block 19. If a "U" shaped tool is placed over the two spring pins 276 on the left in FIG. 45 and pushed into and toward the right, both spring pins 276 can be depressed at the same time until they clear the inside edge of the jaw holder 16 on the left. With both of the spring pins 276 depressed at the same time, the lower jaw 7 can be removed by pulling it up and out of the two jaw holders 16. Since there is a different lower jaw 7 for each of the Ranges 0 through 4 then the lower jaws 7 can be easily changed and snapped in place to match the specific range of the conductor size selected.

Figure 47:
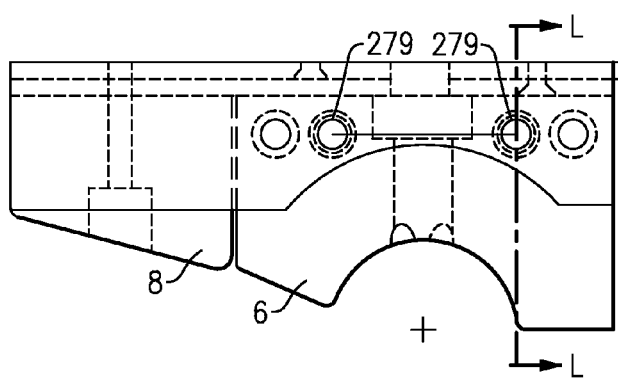
FIG. 47 illustrates a right side view of the upper snap-in jaw for range 4.
Figure 48:
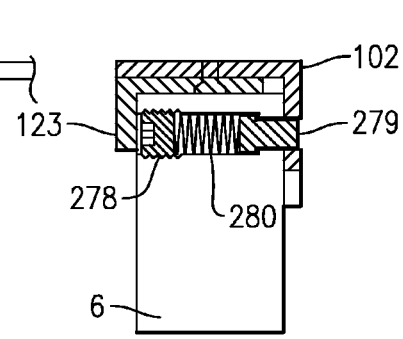
FIG. 48 illustrates a sectional view taken along line L-L of FIG. 47.

Likewise a similar design is employed for the two upper jaws 6 shown in FIGS. 47-48. Although spring pin 279 and spring 280 are different from those used for the lower jaw 7, the concept of depressing the spring pins 279 with a "U" shaped tool and removing the upper jaws 6 is the same. Here again, two upper jaws 6 are needed for each Range 0 through 4 to span the complete range of conductor diameter sizes. This "snap-in" jaw design makes it easy to remove and adjust the temperature sensor probe assembly 273 and the ring nut 270 as shown in FIG. 22 to set the vertical position of the temperature sensor probe assembly 273. The jaw insert 8 is never removed when changing the upper "snap-in" jaws 6.

The preceding description is exemplary rather than limiting in nature. Variations and modifications to the disclosed examples may become apparent to those skilled in the art that do not necessarily depart from the essence of this disclosure. The scope of legal protection given to this disclosure can only be determined by studying the following claims.

The invention claimed is:

1. A device for attaching to a power line conductor comprising:
   a jaw assembly; and
   at least one jaw slot formed on a portion of the jaw assembly configured to engage a stranded power line conductor, wherein the at least one jaw slot extends at an angle on the jaw assembly configured to match a helical angle of the strands on an outer surface of the stranded power line conductor and configured to space the jaw assembly from at least one strand of the stranded power line conductor.

2. The device of claim 1 wherein the jaw slot is semicircular in shape and has a width greater than a diameter of at least one of the strands of the stranded power line conductor.

3. The device of claim 1 wherein the jaw assembly includes at least one upper jaw and at least one lower jaw configured to engage the stranded power line conductor.

4. The device of claim 3 wherein the jaw slot is located on at least one of the at least one upper jaw or the at least one lower jaw with the helical angle being approximately 14 degrees.

5. The device of claim 1 wherein the jaw assembly includes two spaced apart upper jaws and at least one lower jaw, each of the two upper jaws including at least one jaw slot formed on a surface configured to engage the stranded power line conductor and extending in a helical direction of approximately 14 degrees.

6. The device of claim 5 wherein the two spaced apart upper jaws are mounted above the at least one lower jaw.

7. The device of claim 1 including at least one pocket formed in the jaw assembly, each of the at least one pocket extending into a corresponding one of the at least one jaw slot and configured to accept a conductor temperature sensor probe.

8. The device of claim 7 including a conductor temperature sensor probe assembly located in the pocket and configured to engage the stranded power line conductor.

9. A device for attaching to a power line conductor comprising:
a jaw assembly for engaging a power line conductor, the jaw assembly including at least one upper jaw and at least one lower jaw, the at least one upper jaw including a contact surface for contacting the power line conductor having a first slope, wherein the at least one upper jaw and the at least one lower jaw are configured to clamp onto the power line conductor and the at least one upper jaw includes a jaw slot formed on the contact surface at an angle configured to match a helical angle of a strand on the power line conductor; and
a jaw insert located adjacent the at least one upper jaw, the jaw insert including a second contact surface having a second slope, wherein the first slope is greater than the second slope.

10. The device of claim 9 wherein the helical angle is 14 degrees.

11. The device of claim 9 including at least one "C" loop coil wherein the jaw assembly is configured to align the power line conductor on a vertical centerline of the "C" loop coil and within one half inch of a horizontal centerline of the "C" loop coil.

12. The device of claim 9 wherein the at least one upper jaw includes at least one spring pin configured to secure the at least one upper jaw to the device.

13. The device of claim 12 wherein the at least one lower jaw includes at least one spring pin configured to secure the at least one lower jaw to the device.

14. The device of claim 9, wherein the at least one lower jaw is surrounded by a lower power supply magnetic core configured to engage an upper power supply magnetic core.

15. The device of claim 14 including at least one compression spring configured to compress the upper power supply magnetic core against the lower power supply magnetic core.

16. The device of claim 15 wherein the force applied by the at least one compression spring to the upper power supply magnetic core is equal to or greater than a repulsive force due to the core flux created by a current flowing in the power line conductor.

17. The device of claim 9 including a pocket formed in the at least one upper jaw, the pocket configured to receive a temperature sensor probe assembly.

18. The device of claim 17 wherein the temperature sensor probe assembly is configured to ground the device to a voltage of the power line conductor.

19. The device of claim 17 including a sensor electronics module in communication with the temperature sensor probe assembly and a transmitter-receiver unit configured to transmit temperature data to a remote location.

20. The device of claim 17 wherein the temperature sensor probe assembly includes an electrically conductive and electro magnetically shielded protection tube having a temperature sensor mounted inside and at the bottom an electrically conductive shoe mounted at the bottom and on the outside of the protection tube.

21. The device of claim 20 including isolation slots on the protection tube adjacent the shoe configured to mitigate the flow of heat from being conducted from the power line conductor to an upper part of the protection tube.

22. The device of claim 21 including a thermally insulated isolation washer surrounding the protection tube that seats on top of the shoe and a compression spring placed over the protection tube which seats on top of the isolation washer and is compressed between the top of the isolation washer and a threaded nipple which in turn is mounted to an upper jaw holder and keeper.

23. The device of claim 22 including a ring nut placed over the shoe and the compression spring that is threaded onto the bottom of the threaded nipple which seats against the bottom of the upper jaw holder and keeper for adjusting the temperature sensor probe assembly in a first or second direction to maintain constant pressure of the temperature sensor probe assembly on the power line conductor.

24. The device of claim 23 including an adjustment spring surrounding the threaded nipple, wherein the threaded nipple is located in a hole in the upper jaw keeper and holder and secured with a bottom ring nut threaded onto the threaded nipple that seats under the upper jaw holder and keeper.

* * * * *